(12) United States Patent
Santangelo

(10) Patent No.: US 8,785,615 B2
(45) Date of Patent: Jul. 22, 2014

(54) SINGLE MOLECULE SENSITIVE PROBES FOR DETECTING RNA

(75) Inventor: Philip J. Santangelo, Winder, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 205 days.

(21) Appl. No.: 13/258,830

(22) PCT Filed: Mar. 25, 2010

(86) PCT No.: PCT/US2010/028670
§ 371 (c)(1),
(2), (4) Date: Sep. 22, 2011

(87) PCT Pub. No.: WO2010/111494
PCT Pub. Date: Sep. 30, 2010

(65) Prior Publication Data
US 2012/0107798 A1    May 3, 2012

Related U.S. Application Data

(60) Provisional application No. 61/163,292, filed on Mar. 25, 2009.

(51) Int. Cl.
*C07H 21/00* (2006.01)
*C07H 21/02* (2006.01)
*C07H 21/04* (2006.01)

(52) U.S. Cl.
CPC ............... *C07H 21/00* (2013.01); *C07H 21/02* (2013.01); *C07H 21/04* (2013.01)
USPC ............... 536/24.3; 536/24.31; 536/24.32

(58) Field of Classification Search
CPC ........ C07H 21/00; C07H 21/02; C07H 21/04; C12N 15/00
See application file for complete search history.

(56) References Cited

U.S. PATENT DOCUMENTS

2005/0287548 A1    12/2005    Bao et al.
2006/0040286 A1 *   2/2006    Mirkin et al. ............... 435/6

OTHER PUBLICATIONS

Santangelo, Philip, "Nanostructured Probes for RNA Detection in Living Cells", Annals of Biomedical Engineering, vol. 34, No. 1, Jan. 1, 2006, pp. 39-50.
"Labeling Oligonucleotides and Nucleic Acids", Molecular Probe Handbook Section 8.2, Sep. 26, 2003, 7 pgs., Accessed Online at http://web.archive.org/web/20030926181637/www.molecularprobes.com/handbook/sections/0802. html.
Nitin, Nitin et al., "Peptide-Linked Molecular Beacons for Efficient Delivery and Rapid mRNA Detection in Living Cells", Nucleic Acids Research, vol. 32, No. 6, Apr. 14, 2004, pp. 1-8.
Santangelo, Philip J. et al., "Dynamics of Filamentous Viral RNPs Prior to Egress", Nucleic Acids Research, vol. 35, No. 11, May 7, 2007, pp. 3602-3611.
Santangelo, Philip J. et al., "Single Molecule-Sensitive Probes for Imaging RNA in Live Cells", Nature Methods, vol. 6, No. 5, Apr. 6, 2009, pp. 347-351.
International Search Report and Written Opinion dated May 27, 2010 for related PCT Application No. PCT/US2010/028670.

* cited by examiner

*Primary Examiner* — James Martinell
(74) *Attorney, Agent, or Firm* — Troutman Sanders LLP; Ryan A. Schneider; Andrew Regan

(57) ABSTRACT

The various embodiments of the present disclosure relate generally to single molecule sensitive probes for detecting RNA, and more particularly to multivalent fluorescent probes for detecting a single molecule of RNA in a cell. The present invention includes a RNA imaging probe comprising: a multivalent core comprising a plurality of attachment sites; a plurality of RNA/DNA chimeric oligonucleotides having a specificity for a target RNA, wherein a RNA/DNA chimeric oligonucleotide is bound to an attachment site of the multivalent core; and a plurality of fluorophores, wherein a fluorophore is bound to the RNA/DNA chimeric oligonucleotide.

32 Claims, 15 Drawing Sheets

Figures 1a-e
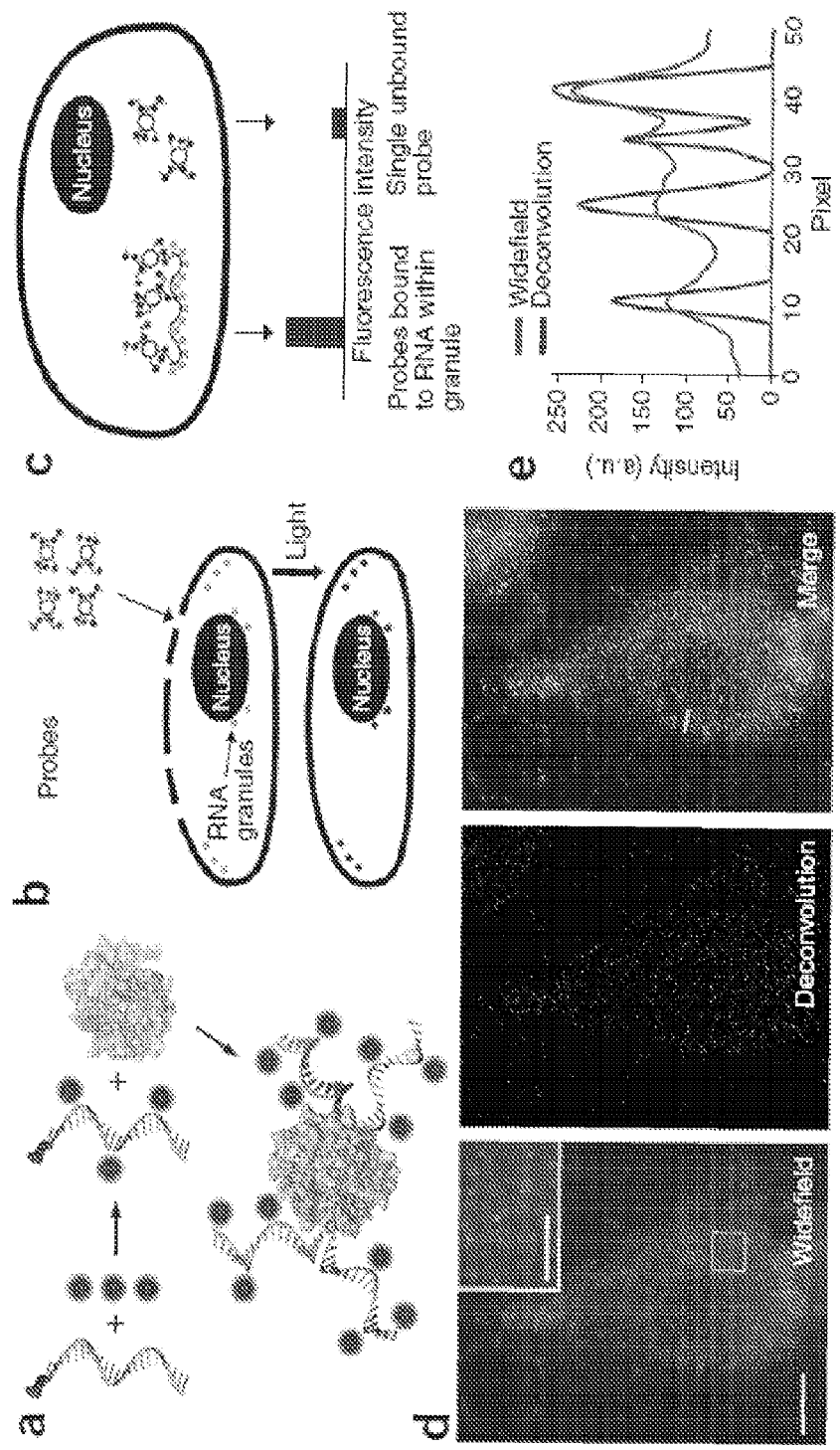

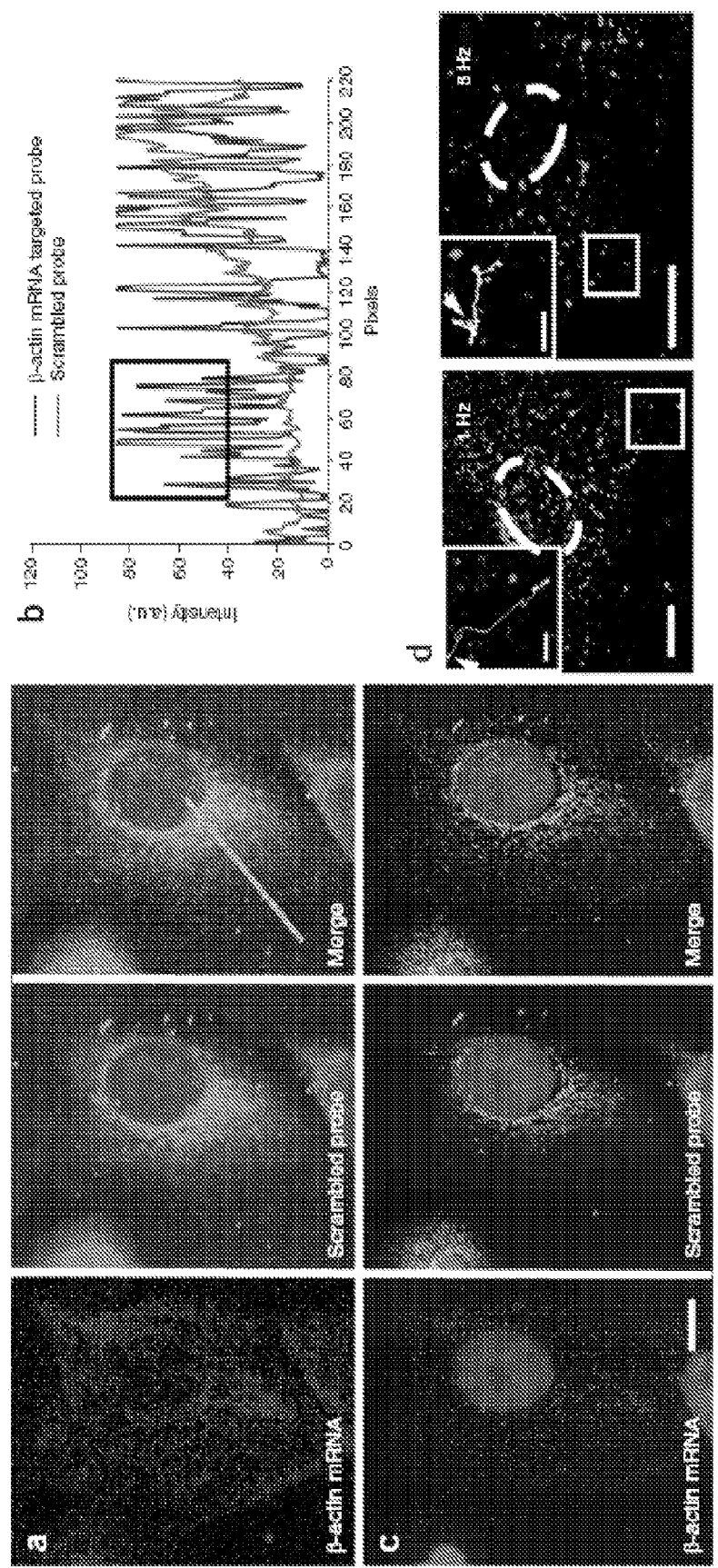
Figures 2a-d

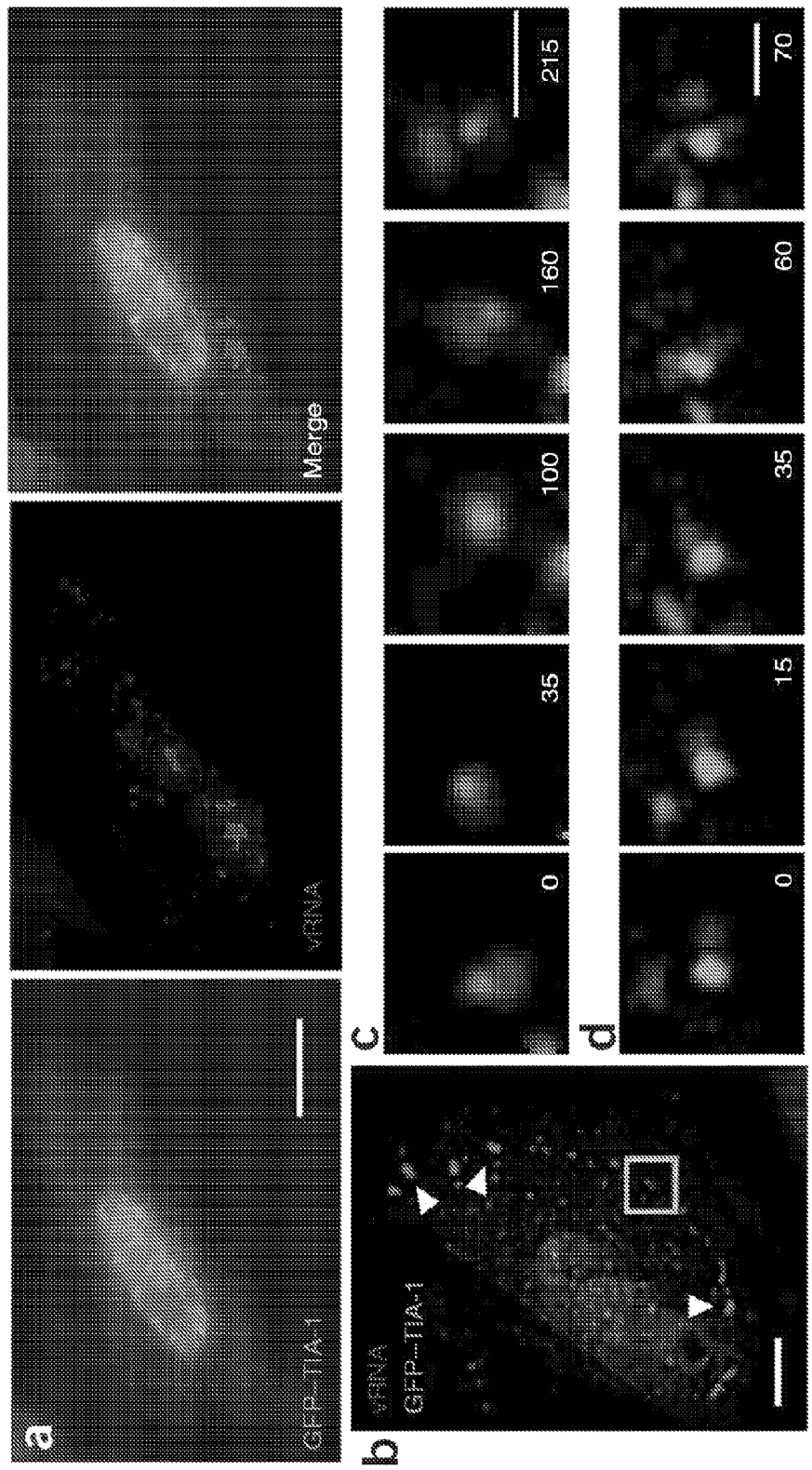
Figures 3a-d

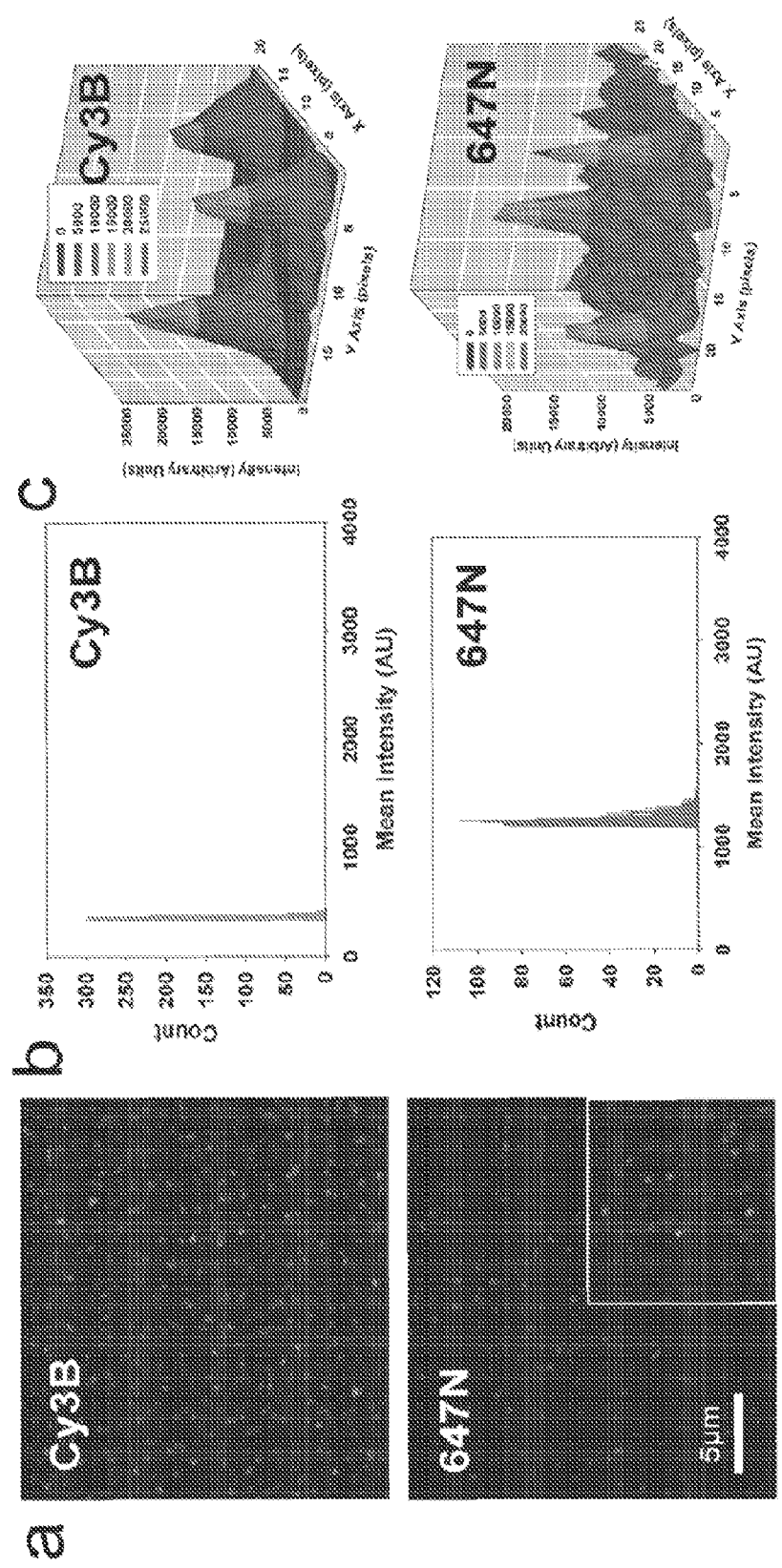
Figures 4a-c

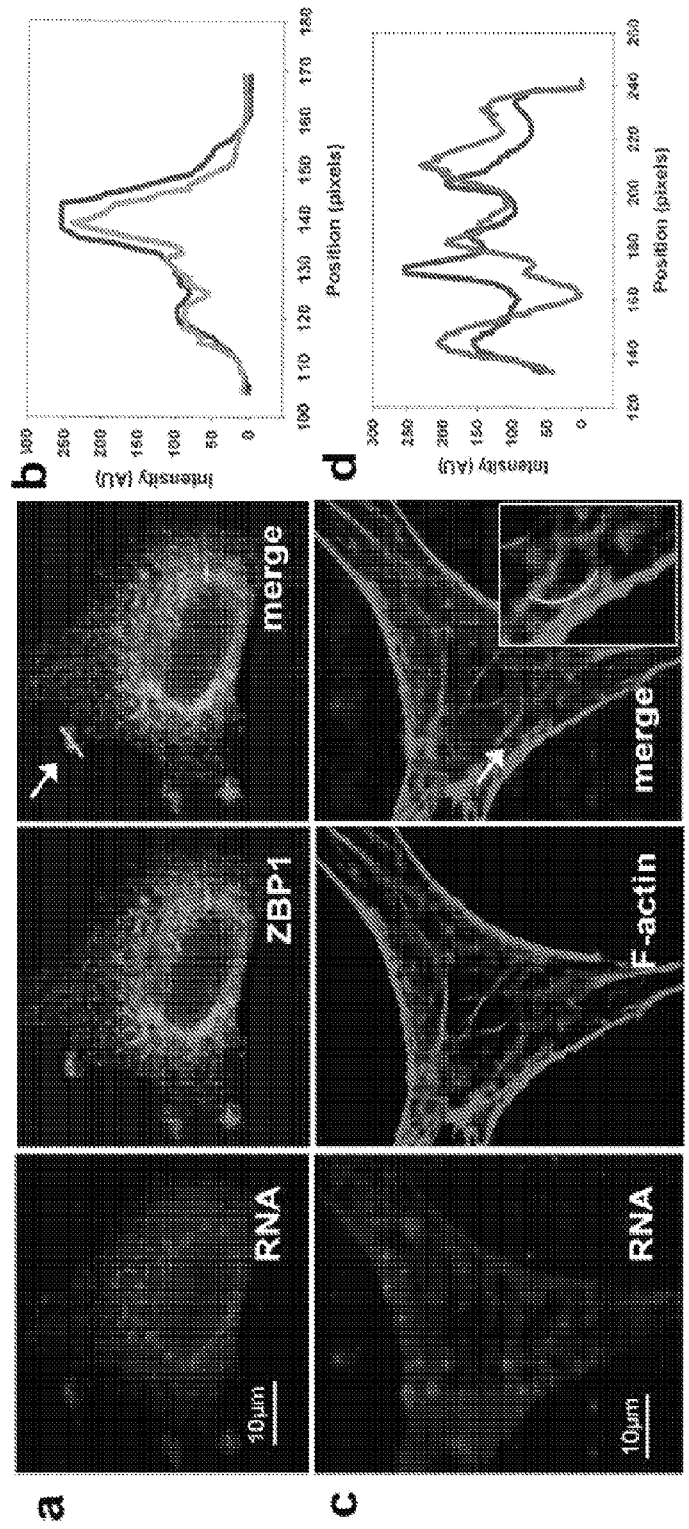
Figures 5a-d
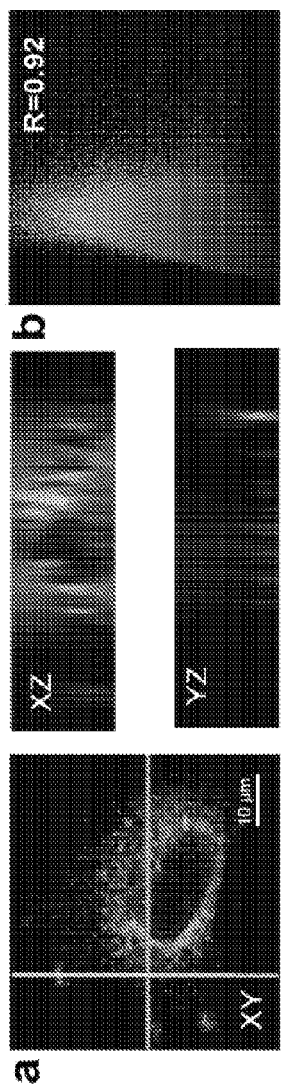
Figures 6a-b

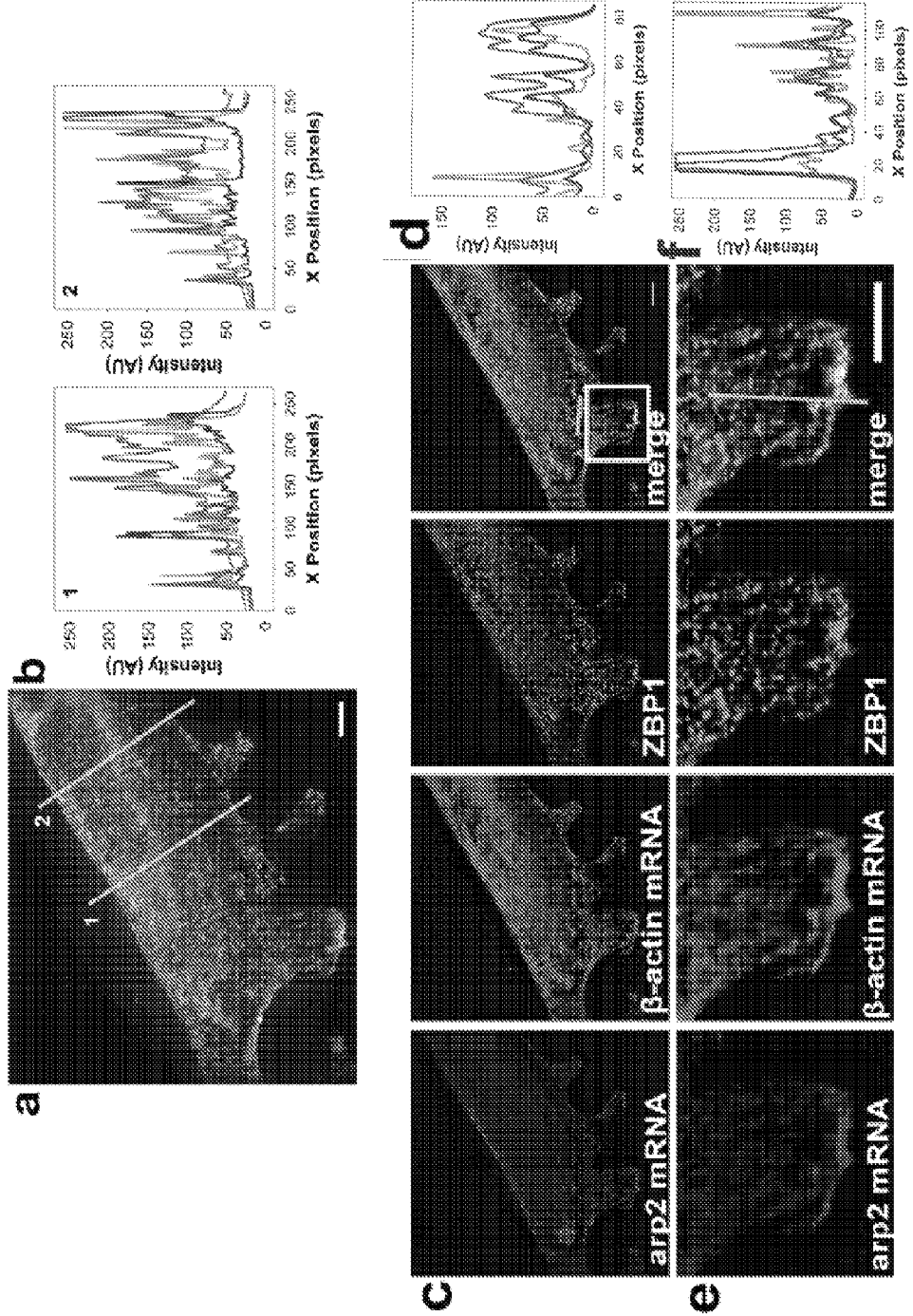
Figures 7a-f

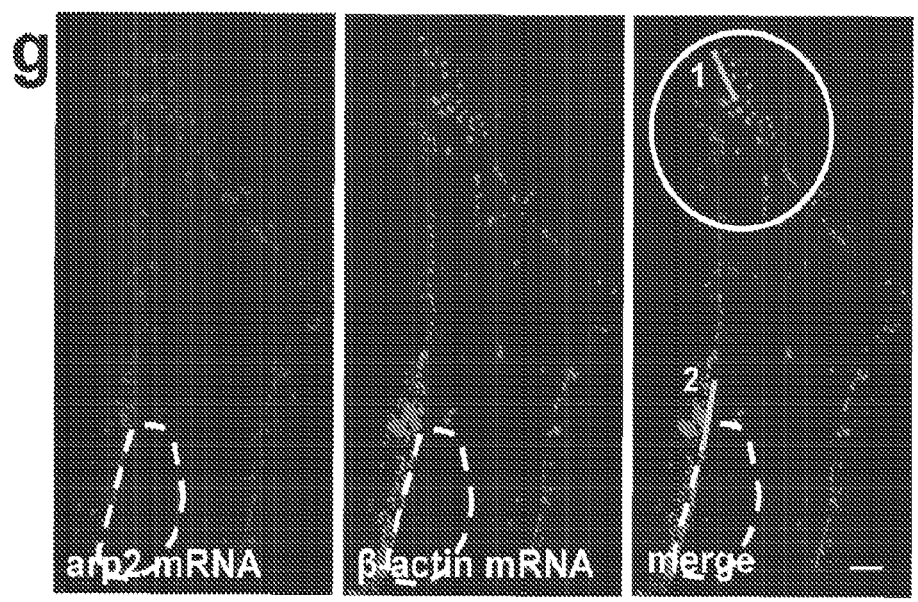
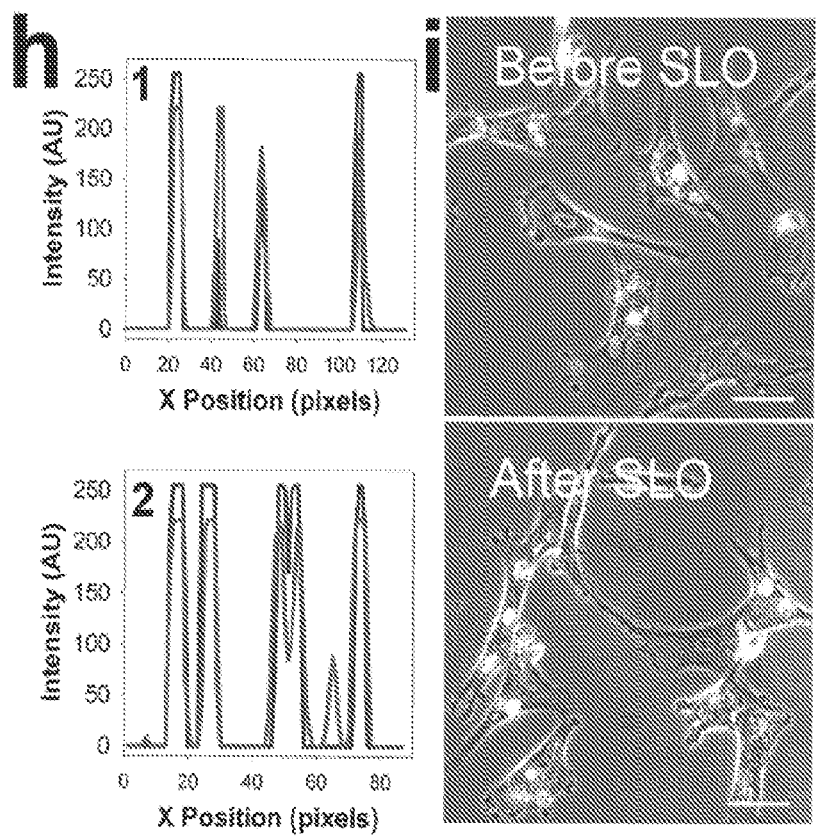
Figures 7g-i

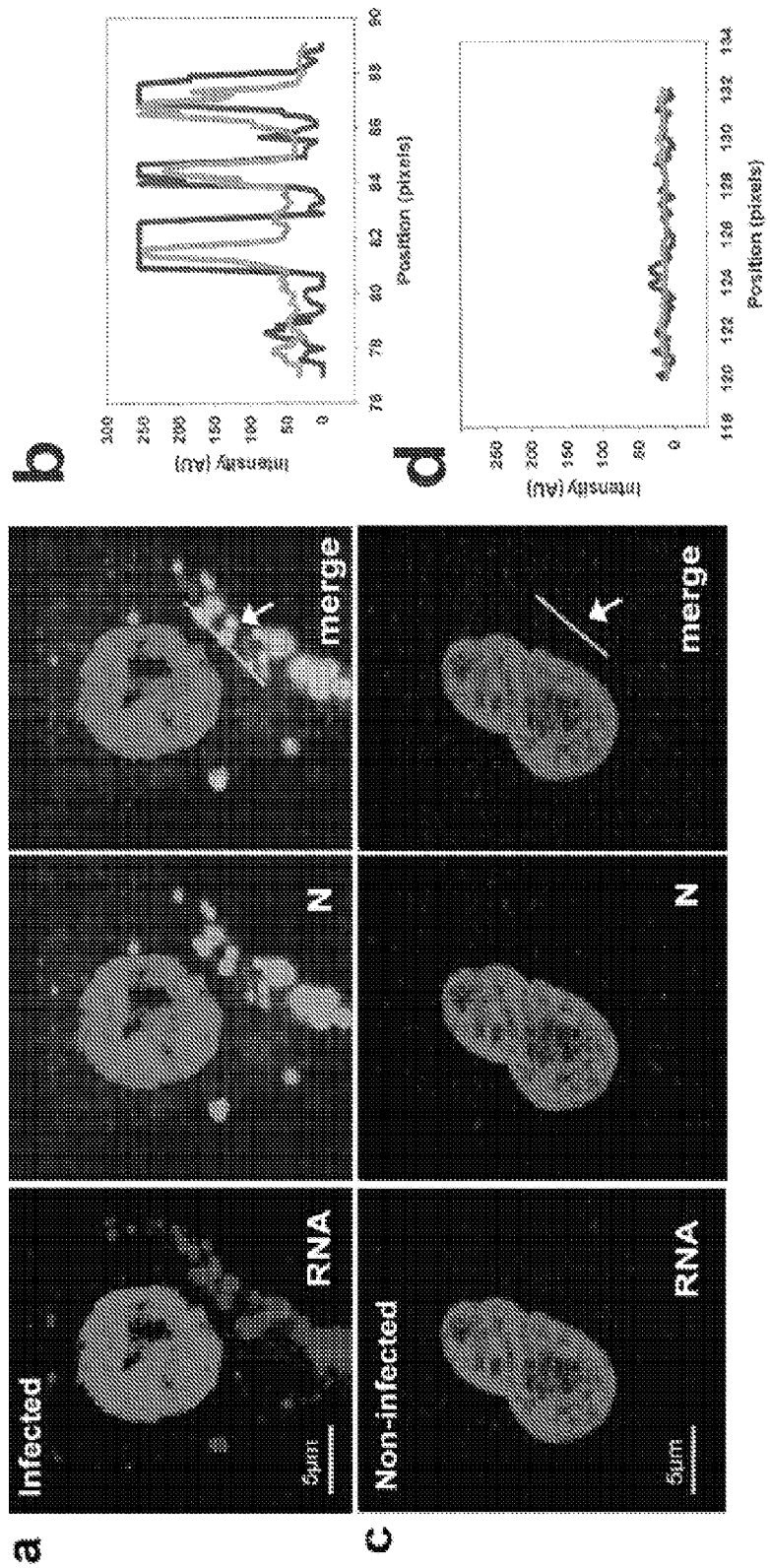
Figures 8a-d

Figures 9a-b
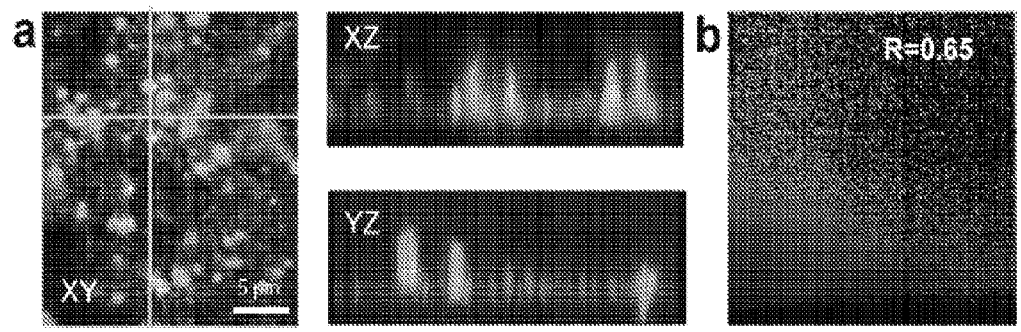
Figures 10a-b
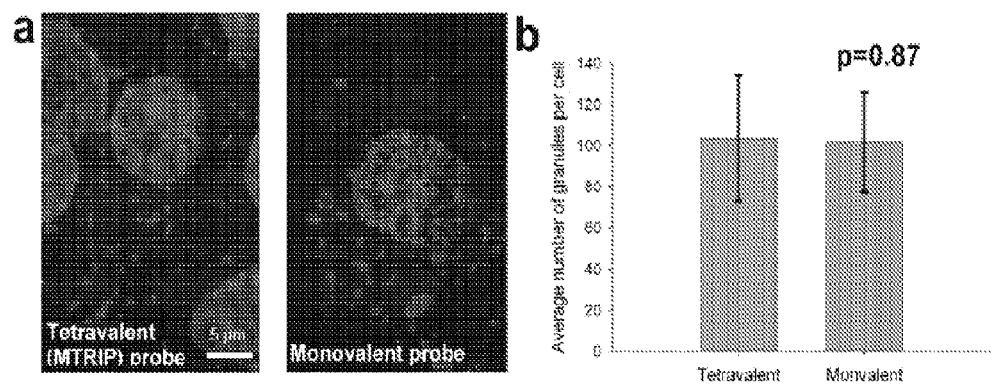
Figure 11
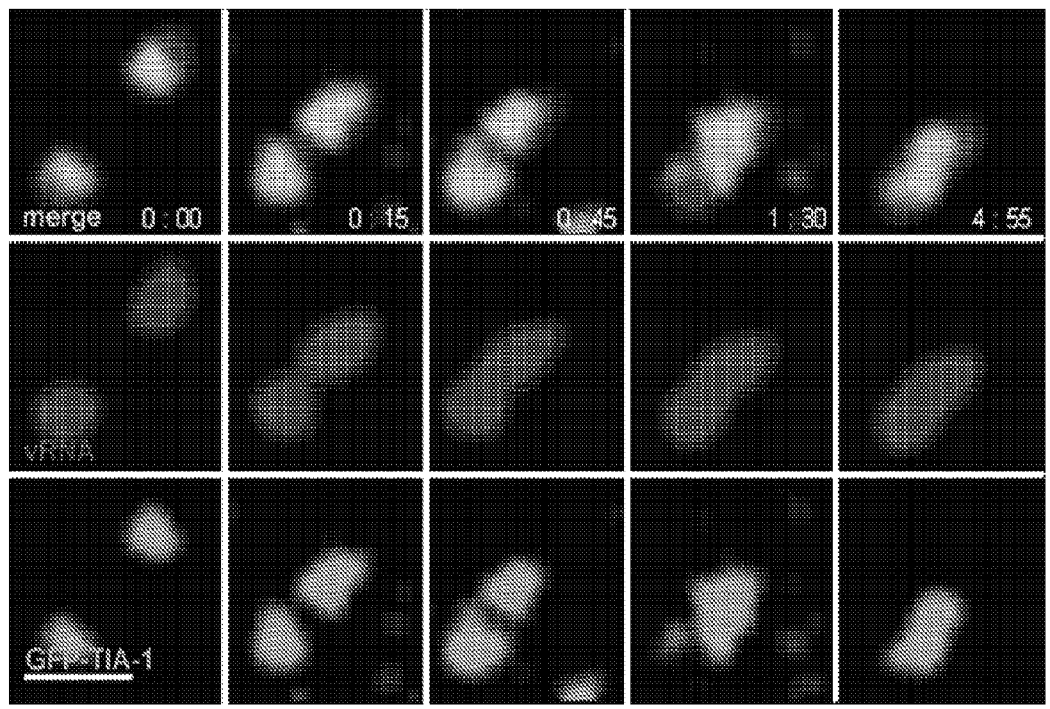

Figure 12
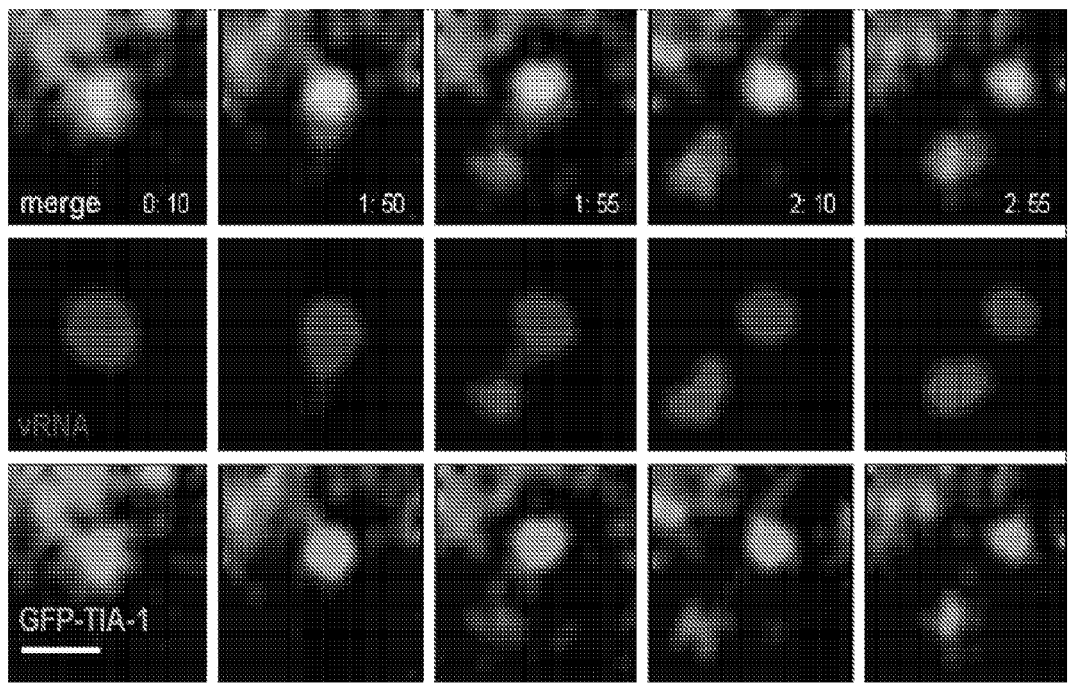
Figure 13
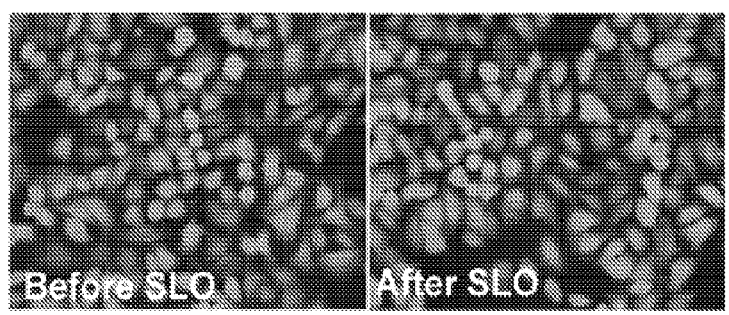
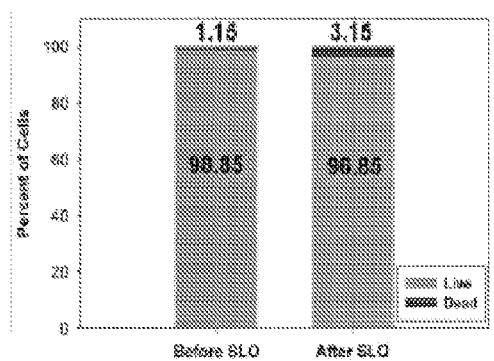

Figures 14a-d
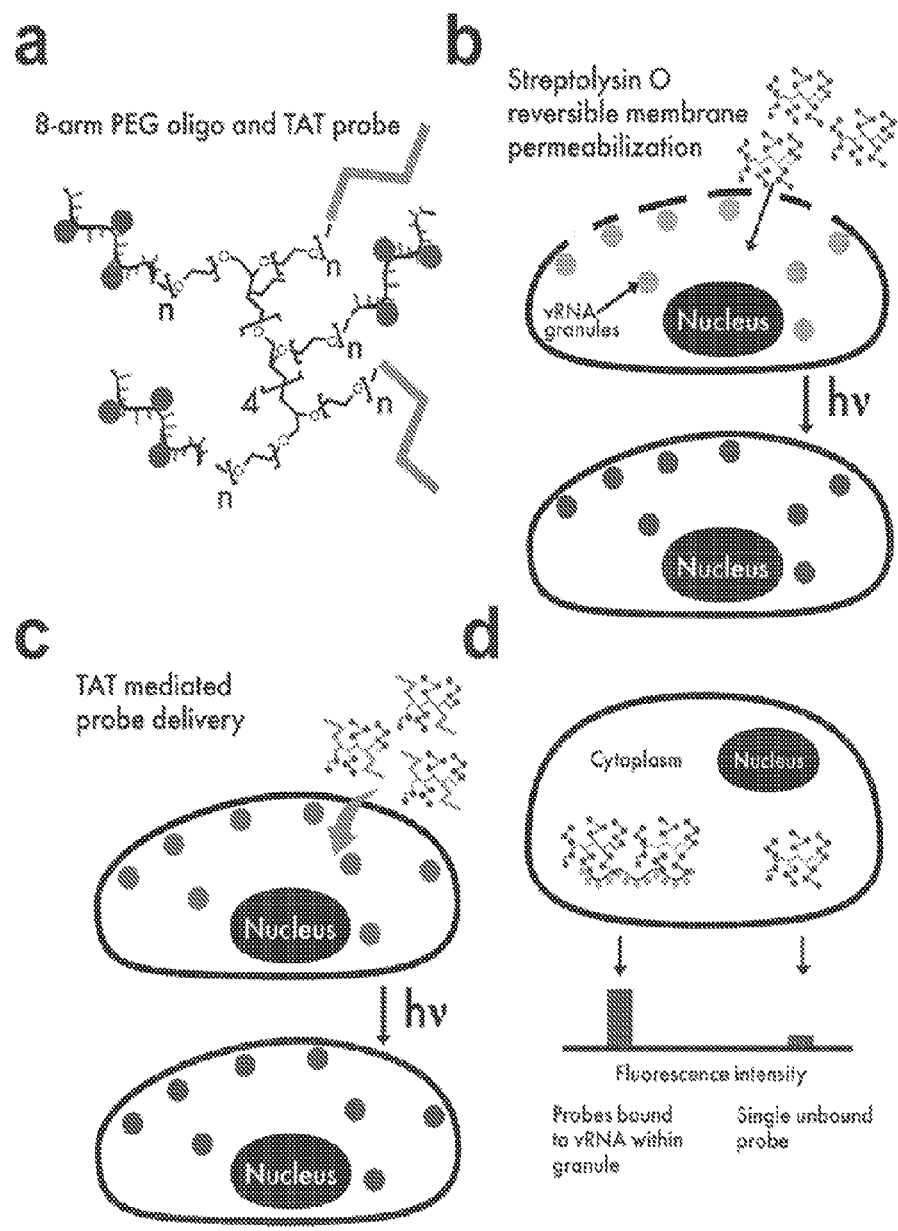

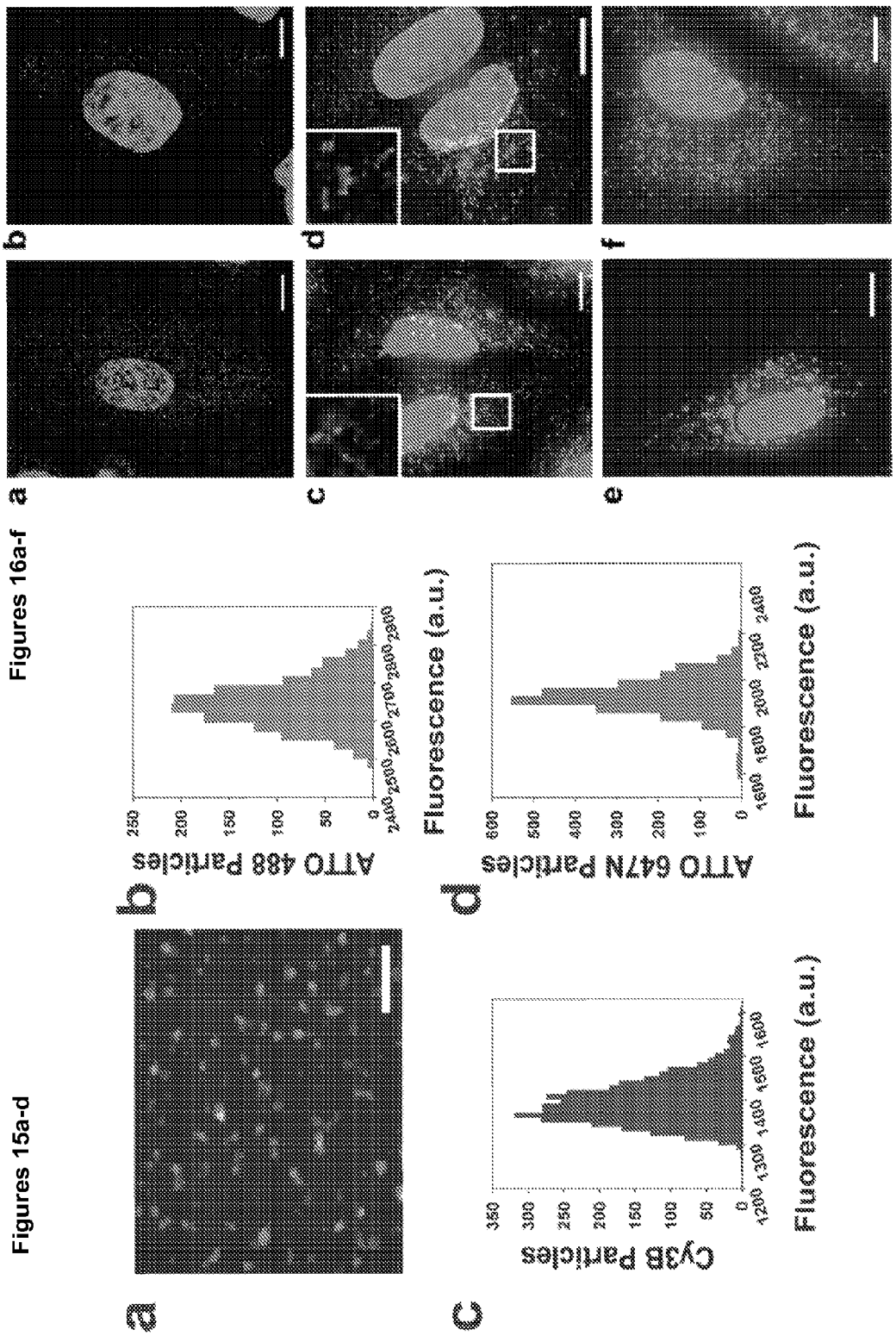

Figures 17a-f
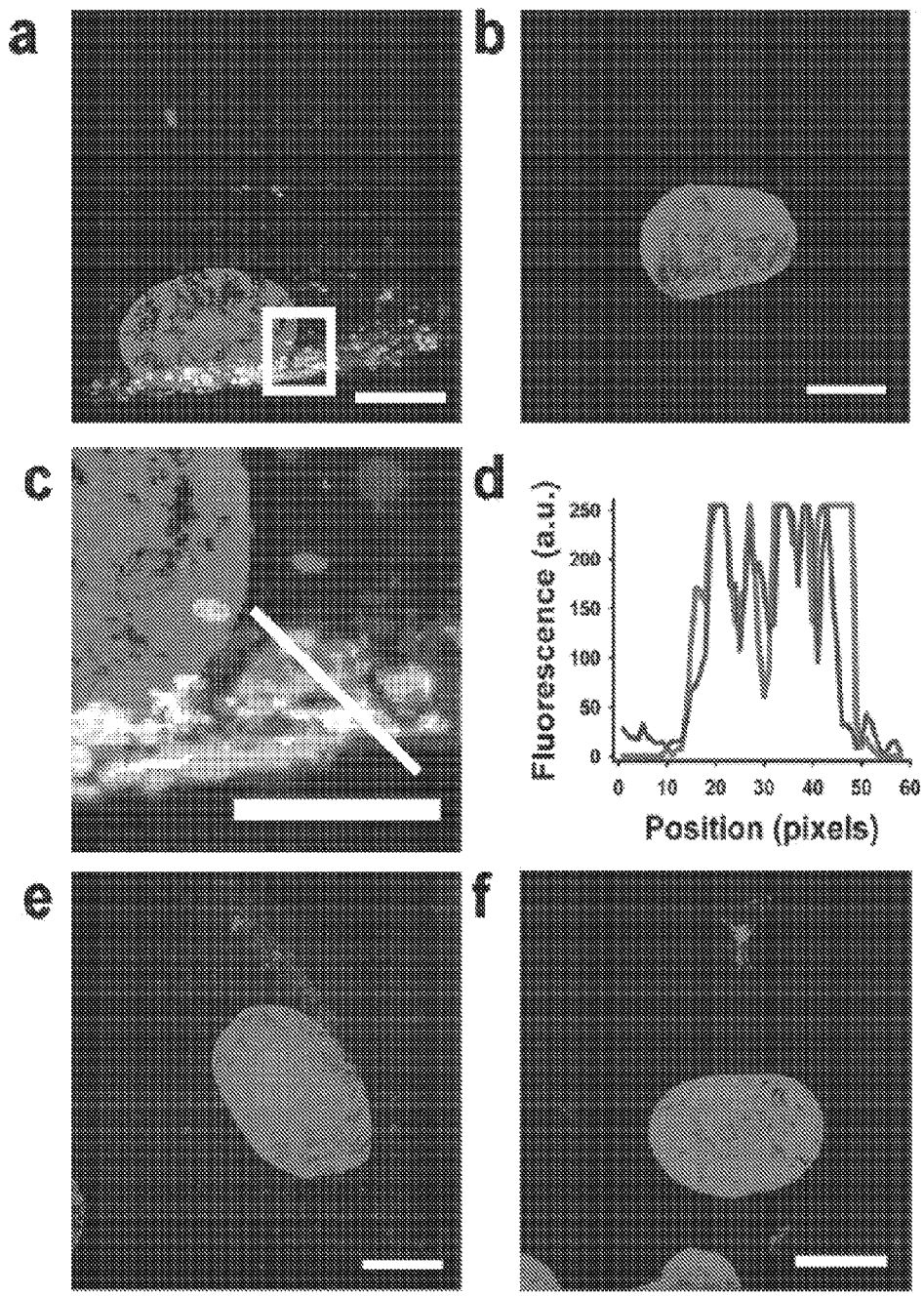

Figures 18a-f
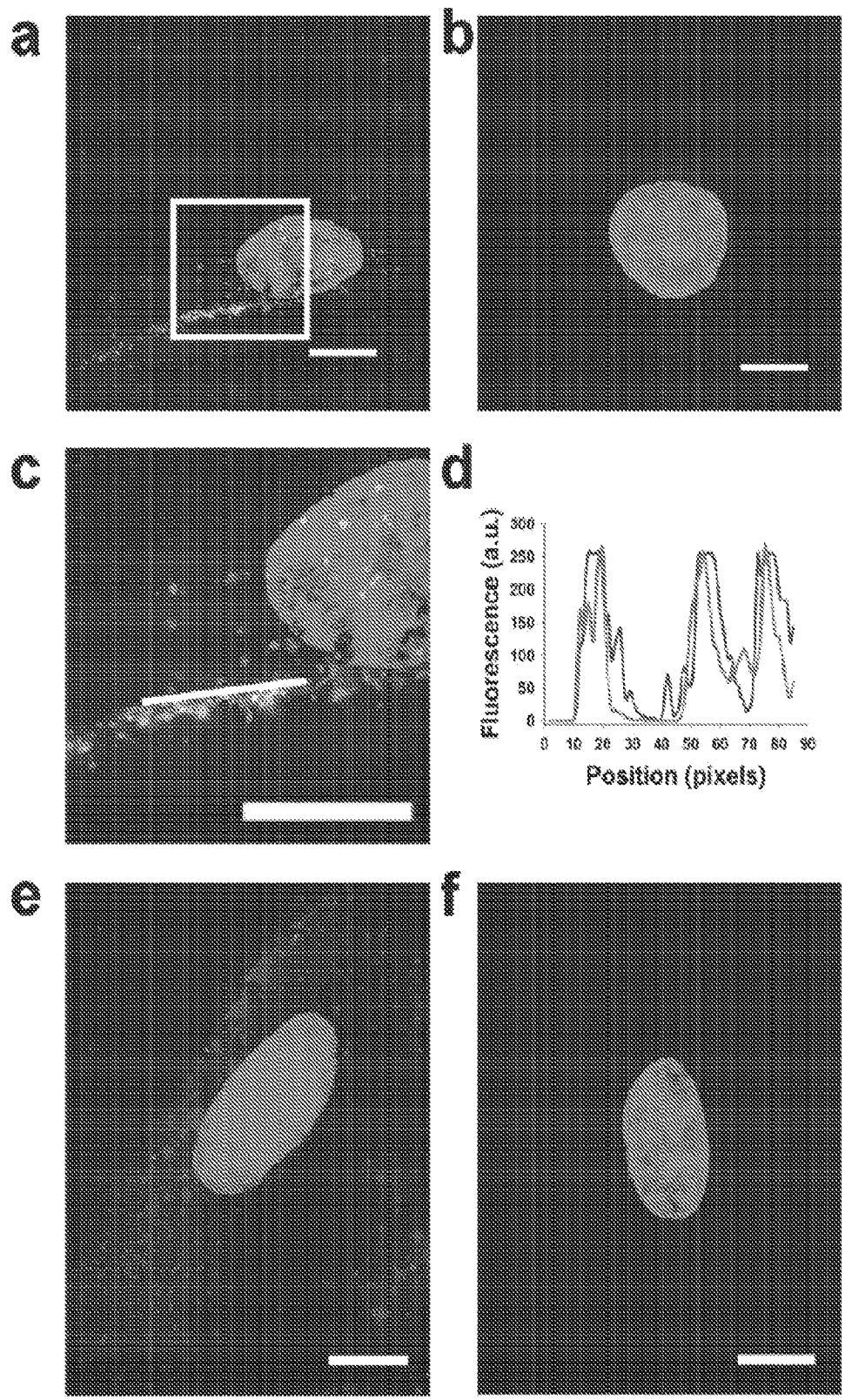

Figures 19a-d

SINGLE MOLECULE SENSITIVE PROBES FOR DETECTING RNA

CROSS-REFERENCE TO RELATED APPLICATIONS

This application claims, under 35 U.S.C. §119, the benefit of International Patent Application Serial Number PCT/US2010/028670, filed 25 Mar. 2010, which claims the benefit of U.S. Provisional Application Ser. No. 61/163,292, filed 25 Mar. 2009, both of which are hereby incorporated by reference in their entirety as if fully set forth below.

BACKGROUND OF THE INVENTION

1. Technical Field

The various embodiments of the present disclosure relate generally to single molecule sensitive probes for detecting RNA. More specifically, the various embodiments of the present disclosure are directed to multivalent fluorescent probes for detecting a single molecule of RNA in a living or fixed cell or tissue.

2. Description of Related Art

In recent years, the imaging of RNAs in live cells has garnered growing attention with a variety of interesting methods developed for this purpose. This research has been driven by the increased appreciation for the role of post-transcriptional regulation on the function of RNA molecules, the role of genomic RNA in viral assembly, and the cellular stress response in pathogenesis.

Various technologies and methodologies have been developed to study intracellular RNA biology in live cells including: plasmid-based systems, where the fluorescent tag and/or the RNA to be tagged are expressed within the cell, or systems based on exogenous RNA-targeting fluorescent probes, which when introduced into the cell, bind to their target via Watson-Crick base pairing. Currently, expressing both the RNA and a fluorescent tag using a plasmid-based system is the state-of-the-art in this field.

Three strategies using plasmid expressed probes have been demonstrated in mammalian cells: (1) a GFP-MS2 fusion protein probe, which binds to multiple binding sites encoded in an expressed target RNA; (2) GFP-RNA binding peptide fusion probes, which bind to a 15 nucleotide RNA hairpin encoded in the expressed target RNA; and (3) probes composed of Pumilio homology domains (PUM-HD) fused to sections of split EGFP, which target two closely spaced 8 nucleotide endogenous sequences. These systems have been used to study cytoplasmic, nuclear mRNA and mitochondrial RNA. A fourth technique, which is an extension of the first three, introduces an exogenous probe, a microinjection-delivered molecular beacon that targets multiple binding sites in an expressed target mRNA.

Employing plasmid-derived probes and RNA give these methods tremendous flexibility but they have limitations. First, they can only be used in cell types that allow for efficient transfection. Second, plasmid-derived mRNA often lack introns, both the correct number and position and the exact 3'-untranslated region (UTR) sequence, which can strongly influence mRNA translational efficiency, decay, and stability. In the case of viral RNA, additions to viral genomes affect replication efficiency, assembly, and viral egress. In addition, plasmid-derived RNAs are often overexpressed, changing the fundamental stoichiometry underlying the RNAs expression. Therefore, it is advantageous to target endogenous RNA in order to improve RNA biology studies. Of the techniques mentioned above, only the PUM-HD fusions and the molecular beacon approach have the ability to study endogenous or non-engineered RNAs, but neither have achieved single molecule sensitivity with endogenous targets.

When imaging endogenous RNA, the sensitivity of the probe is extremely important. First, mRNA is not highly abundant within cells, and second, RNA function is governed by the set of highly abundant proteins that interact with it. The difference in their concentrations makes studying these interactions via imaging very difficult. Therefore, RNA probes must be sensitive enough to detect a small number of RNAs within a sea of proteins. In order to achieve single molecule sensitivity, the above techniques require the binding of many probes; for example, binding sites for up to 50 MS2-GFP molecules or 96 molecular beacon molecules are necessary. Given both the additions to the RNA and the size of the probes, large molecular weight additions are required to achieve single molecule sensitivity. These additions could have effects on both RNA localization and dynamics. Further, for probe-based methods, delivery into the correct cellular compartment is critical in order for the probes to bind rapidly to their target. Delivery methods that result in accumulation of probe in the nucleus of cells or utilize endocytic vesicles can lead to nonspecific signal and degradation of the probe.

In order to make an advance in the area of RNA imaging, new techniques must be capable of imaging endogenous RNA, have single molecule sensitivity, allow for the imaging of multiple RNAs, and minimize the number and molecular weight of probes binding to the RNA. It is to the provision of such RNA imaging techniques that the various embodiments of the present invention are directed.

BRIEF SUMMARY OF THE INVENTION

Various embodiments of the present invention are directed to single molecule sensitive probes for detecting RNA. More specifically, the various embodiments of the present disclosure are directed to multivalent fluorescent probes for detecting a single molecule of RNA in a living or fixed cell or tissue.

An aspect of the present invention includes a biomolecule probe comprising: a multivalent core comprising a plurality of attachment sites; a ligand having specificity for a target, wherein the ligand is bound to an attachment site of the multivalent core; and a reporter molecule, wherein the reporter molecule is bound to the ligand. The ligand can comprise a plurality of ligands, and a ratio of the plurality of ligands to the plurality of attachment sites on the multivalent core can be equal to or less than about 1. The reporter molecule can comprise a plurality of reporter molecules, and a ratio of reporter molecule to ligand is greater than or equal to about 1. The target can be one or more biomolecules, for example a RNA.

In one embodiment of the present invention, the ligand can comprise a nucleic acid. The nucleic acid can comprises an attachment region, a spacer region, and a hybridization region. Within one or more of any of these regions, the nucleic acid can include a moiety sufficient to bind a reporter molecule. In some embodiments, the reporter molecule can comprise a fluorophore. In an exemplary embodiment, the ratio of reporter molecule (e.g., fluorophore) to ligand is equal to about 3. The multivalent core can be made of many materials, such as avidin or a derivative thereof or a multivalent polyethylene glycol core. In various embodiments of the present invention, the biomolecule probe can further comprise a targeting moiety, an epitope moiety, or a combination thereof.

Another aspect of the present invention includes a RNA imaging probe comprising: a multivalent core comprising a plurality of attachment sites; a plurality of RNA/DNA chimeric oligonucleotides having a specificity for a target RNA, wherein a RNA/DNA chimeric oligonucleotide is bound to an attachment site of the multivalent core; and a plurality of fluorophores, wherein a fluorophore is bound to the RNA/DNA chimeric oligonucleotide. The ratio of fluorophore to RNA/DNA chimeric oligonucleotide can be greater than 1. In an exemplary embodiment of the present invention, the ratio of fluorophore to RNA/DNA chimeric oligonucleotide is greater than or equal to about 3. The RNA/DNA chimeric oligonucleotide can comprise an attachment region, a spacer region, and a hybridization region. The multivalent core can comprise a tetravalent strepavidin core, and the attachment region of the RNA/DNA chimeric oligonucleotide can comprise biotin. Alternatively, the multivalent core can comprise a multivalent polyethylene glycol core, and the attachment group can comprise a 5' thiol modified 2'-O-methyl uridine. The spacer region can comprise a plurality of deoxythymidines, a plurality of deoxyadenonsines, or combinations thereof. In an exemplary embodiment, the RNA/DNA chimeric oligonucleotide further comprises a plurality of amino-modified deoxythymidines. The RNA imaging probe of the present invention can further comprise a targeting moiety, an epitope moiety, or a combination thereof.

Another aspect of the present invention includes a method for detecting a single molecule of RNA using a RNA imaging probe comprising: delivering an effective amount of the RNA imaging probe to a cell; and detecting a molecule of a target RNA in a cell. The effective amount of an RNA imaging probe has a concentration of less than about 1 micromolar ($\mu$M), and preferably a concentration ranging from about 5 nanomolar (nM) to about 30 nanomolar (nM). The delivering an effective amount of an RNA imaging probe to a cell can comprise permeabilizing the cell with streptolysin O or microinjecting the RNA imaging probe into a cell. The detecting a molecule of a RNA in a cell can comprise visualizing the association of the RNA imaging probe with the molecule of a target RNA in a cell through microscopy. The target RNA can be a native, non-engineered RNA, such as for example a cellular RNA or a viral RNA. The methods of the present invention can further comprise detecting a protein that is associated with the target RNA.

Other aspects and features of embodiments of the present invention will become apparent to those of ordinary skill in the art, upon reviewing the following description of specific, exemplary embodiments of the present invention in conjunction with the accompanying figures.

BRIEF DESCRIPTION OF DRAWINGS

FIG. 1a is a schematic of a multiply labeled tetravalent RNA imaging probe (MTRIPs), where fluorophores (spheres) are conjugated to amino-modified chimera oligonucleotides (helices) and bound to streptavidin.

FIG. 1b is a schematic of cells, permeabilized with streptolysin O, where probes were allowed to diffuse through pores followed by rapid binding of the probes to targets, which was visualized after light stimulation.

FIG. 1c demonstrates that single RNAs bound to multiple probes were recognized by the enhanced signal-to-background ratio.

FIG. 1d illustrates live-cell widefield, deconvolved, and merged images of a single optical plane of Cy3B-labeled hRSV-targeted probes in a noninfected A549 cell. Scale bars, 10 $\mu$m (2.5 $\mu$m in inset, which is a magnification of the boxed region).

FIG. 1e provides an intensity profile of widefield (gradual curve) and deconvolved images (distinct peaks) in the line of the merge image of FIG. 1d.

FIG. 2a illustrates $\beta$-actin mRNA and a 'scrambled' probe imaged with a laser scanning confocal microscope where all image planes are represented.

FIG. 2b provides intensity profiles along the line in FIG. 2a. The box highlights the large numbers of $\beta$-actin mRNA individual granules at the cell periphery detected by the targeted probe, but not by the scrambled probe.

FIG. 2c illustrates a single optical plane of the same cell as in FIG. 2a resulting from widefield-deconvolution imaging. Scale bar, 5 $\mu$m.

FIG. 2d illustrates a single optical plane of two living A549 cells (nucleus denoted with dashed line) imaged at 1 Hz for 3 mM and 5 Hz for 30 s, respectively. Inset, images of boxed regions, including traces of $\beta$-actin mRNA granule trajectories for 70 s (1 Hz) and 30 s (5 Hz). Starting points are denoted by arrows. Scale bars, 10 $\mu$m (3 $\mu$m in insets).

FIG. 3a shows fluorescence images of a live A549 cell imaged 24 h after infection and 48 h after transfection, showing no stress granules. Scale bar, 10 mm.

FIG. 3b is a live-cell image of a single optical plane of GFP-TIA-1 and Cy3B labeled hRSV-targeted MTRIPs (25 nM) in an A549 cell, 24 h after infection, 48 h after transfection and 20 mM after exposure to 1 mM sodium arsenite. Arrowheads denote stress granules. Scale bar, 10 $\mu$m.

FIG. 3c illustrates time-lapse images of stress granule (green) collision, penetration, and separation of a viral RNA granule (red). All times are given in seconds. Scale bars, 1 $\mu$m.

FIG. 3d provides images of the docking of a stress granule and viral RNA granule, which occurred for only 45 s before separation. All granule interactions shown were imaged in the area denoted by the box in FIG. 3b. All times are given in seconds. Scale bars, 1 $\mu$m.

FIG. 4a illustrates images of single Cy3B and Atto 647N probes, respectively, at 2 nM. Inset depicts image of a mixture of Cy3B and Atto 647N MTRIPs demonstrating probe independence.

FIG. 4b depicts unimodal histograms of the mean intensity within each diffraction-limited spot constructed from 750-1000 detected probes.

FIG. 4c provides three-dimensional intensity profiles of representative probes post-deconvolution, which further demonstrate that single probes were imaged.

FIG. 5a illustrates MTRIPs using human $\beta$-actin probe 1 (red, left panel), delivered at 30 nM, colocalize (yellow, right panel) with ZBP1 (green, center panel), especially in the ends of pseudopods.

FIG. 5b is an intensity profile drawn through one of the pseudopods, which further demonstrates colocalization.

FIG. 5c illustrates the colocalization of $\beta$-actin mRNA with F-actin. MTRIPs (red, left panel) delivered at 1 nM show colocalization (purple, right panel) with phalloidin stained stress fibers (blue, center panel). Inset image within merge focuses on a region of significant colocalization.

FIG. 5d demonstrates an intensity profile of FIG. 5c showing the correlation of F-actin signal (blue) with MTRIPs (red).

FIG. 6a illustrates quantification of 3D colocalization of single (human ($\beta$-actin mRNA probe 1) MTRIP targeted to $\beta$-actin mRNA and ZBP1 in a motile epithelial cell. XY, XZ, and YZ profiles at location designated by the cross-hair are provided as evidence of colocalization within both a pseudopod (YZ) and within the perinuclear region (XZ).

FIG. 6b is a scatter plot of voxel intensities generated from the 3D reconstruction of voxels and the Manders overlap coefficient calculated. In this case, the Manders overlap coefficient was 0.92, suggesting significant colocalization in three dimensions.

FIG. 7a is an extended view of arp2 (red) and β-actin (blue) mRNA, and ZBP1 (green) in a motile primary chicken embryonic fibroblasts CEF. Scale bar represents 5 µm.

FIG. 7b are intensity profiles through two cross-sections (denoted 1 and 2) of the extended view reveal two types of localization; within the perinuclear region, β-actin mRNA signal is not correlated with the arp2 mRNA signal, especially from approximately pixel 100 to 225 in profile 1 and from 100 to 150 and 175 to 225 in profile 2; ZBP1 and β-actin mRNA are correlated within these same regions.

FIGS. 7c-f illustrate a single plane image of the cell, near the glass surface and within a lamellipodium (indicated by the white box). Colocalization of arp2 (red, far left panel) mRNA, β-actin (blue, central left panel) mRNA, and ZBP1 (green, central right panel) can be observed especially within the lamellipodium near the leading edge. Scale bar represents 5 µm.

FIGS. 7g-h is a live cell image and intensity profile, respectively, of arp2 (red, left panel) and β-actin (blue, central panel) mRNA tagged with the same MTRIPs as above; granules within a protrusion of CEF show significant colocalization. The dashed white region represents the cell nucleus. Scale bar represents 5 µm.

FIG. 7i provides phase contrast images of primary CEFs before and after SLO exposure, which shows no significant changes in cellular morphology. The images were taken 20 minutes after streptolysin O (SLO) exposure. Scale bar represents 50 µm.

FIG. 8a-b illustrate that MTRIPs targeted the viral genomic RNA of hRSV (red, right panel) and colocalized (yellow, left panel) with hRSV nucleocapsid protein (green, center panel) in infected cells. DAPI staining stains the nucleus of the cell. Colocalization was observed in the images and quantified in intensity profiles (b) along the line as denoted by the white arrow.

FIGS. 8c-d demonstrate that little background was observed in non-infected cells. Colocalization was observed in the images and quantified in intensity profiles along the line as denoted by the white arrow.

FIGS. 9a-b illustrate quantification of 3D colocalization of MTRIP targeted to hRSV genomic RNA (red) and nucleocapsid protein (green) in an epithelial cell. (a) XY, XZ, and YZ profiles at location designated by the cross-hair are provided as evidence of colocalization. Strong yellow signal representing colocalization can be observed in both cross-sections. (b) From the 3D reconstruction of voxels, a scatter plot of voxel intensities was generated, and the Manders overlap coefficient calculated. In this case the Manders overlap coefficient was 0.65, demonstrating colocalization in three dimensions.

FIGS. 10a-b provide a comparison of tetravalent MTRIPs and noncovalent probes (single multiply-labeled ligand) both targeted to hRSV genomic RNA (red). FIG. 10a provides representative images from infections targeted by each probe type. FIG. 10b demonstrates that RNA granules from over 30 cells for both the tetravalent and monovalent probes were counted via Volocity using the same conditions.

FIG. 11 illustrates time-lapse imaging of granule fusion. Scale bar, 1 µm.

FIG. 12 illustrates time-lapse imaging of granule splitting. Scale bar, 1 µm.

FIG. 13 illustrates a live-dead assay assessment of the effects of SLO on A549 cells.

FIG. 14a is a schematic of an 8-arm PEG conjugated to fluorescently labeled oligonucleotides and TAT peptide (heavy blue line).

FIG. 14b is a schematic of cells, reversibly permeabilized with streptolysin O. Probes diffused into the cytoplasm, bound to target RNA, and were visualized under a fluorescence microscope.

FIG. 14c is a schematic of transduction of a TAT-PEG probe without streptolysin O permeabilization.

FIG. 14d demonstrates that detection of RNA is achieved through the increased signal intensity when multiple probes are bound to a single RNA.

FIG. 15a illustrates that Atto 488 (green), Cy3B (red), and Atto 647N (blue) labeled probes were adsorbed onto glass and analyzed for the colocalization and aggregation. Scale bar is 2 µm.

FIGS. 15b-d depict corresponding intensity histograms of FIG. 15a showing a unimodal distribution consistent with single probes.

FIGS. 16a-f demonstrate distribution of PEG probes targeted against hRSV in A549 cells and colocalization with endosomal marker CD63 and lysosomal marker LAMP1. (a) Probe (red) was delivered by SLO permeabilization, and (b) probe (red) was delivered by TAT conjugation. Extended focus of uninfected cells with probe (red) delivered by TAT conjugation and (c) stained for CD63 (green) and (d) LAMP1 (green). Insets in c and d show single plane from boxed region. Extended focus of hRSV infected cells with probe (red) delivered by TAT conjugation and stained for (e) CD63 (green) and (f) LAMP1 (green). Scale bars are 10 µm.

FIGS. 17a-b demonstrate distribution of probes (red) into fixed hRSV (a) infected and (b) noninfected cells and staining for the viral protein N (green) and DAPI (blue). Scale bar, 10 µm.

FIG. 17c demonstrates magnification of boxed region in FIG. 17a. Scale bar, 5 µm.

FIG. 17d is an intensity profile along line in FIG. 17c.

FIGS. 17e-f illustrate the distribution of probes (red) into live hRSV (e) infected and (f) noninfected cells. Scale bar, 10 µm.

FIGS. 18a-b illustrates the distribution of probes (red) into fixed hRSV (a) infected and (b) noninfected cells and staining for the viral protein N (green) and DAPI (blue). Scale bar, 10 µm.

FIG. 18c illustrates magnification of boxed region in FIG. 18a. Scale bar, 5 µm.

FIG. 18d is an intensity profile along line in FIG. 18c.

FIGS. 18e-f demonstrate the distribution of probes (red) into live hRSV (e) infected and (f) noninfected cells. Scale bar, 10 µm.

FIGS. 19a-d illustrate the absorbance spectra of labeled probes (a) Cy3b-labelled oligonucleotides, (b) Cy3b-labelled oligonucleotides in the PEG probes, (c) Cy3b-labelled oligonucleotides in the PEG-TAT probes, and (d) unlabelled oligonucleotides in the PEG-TAT-FAM probes.

DETAILED DESCRIPTION OF THE INVENTION

Figure 20:
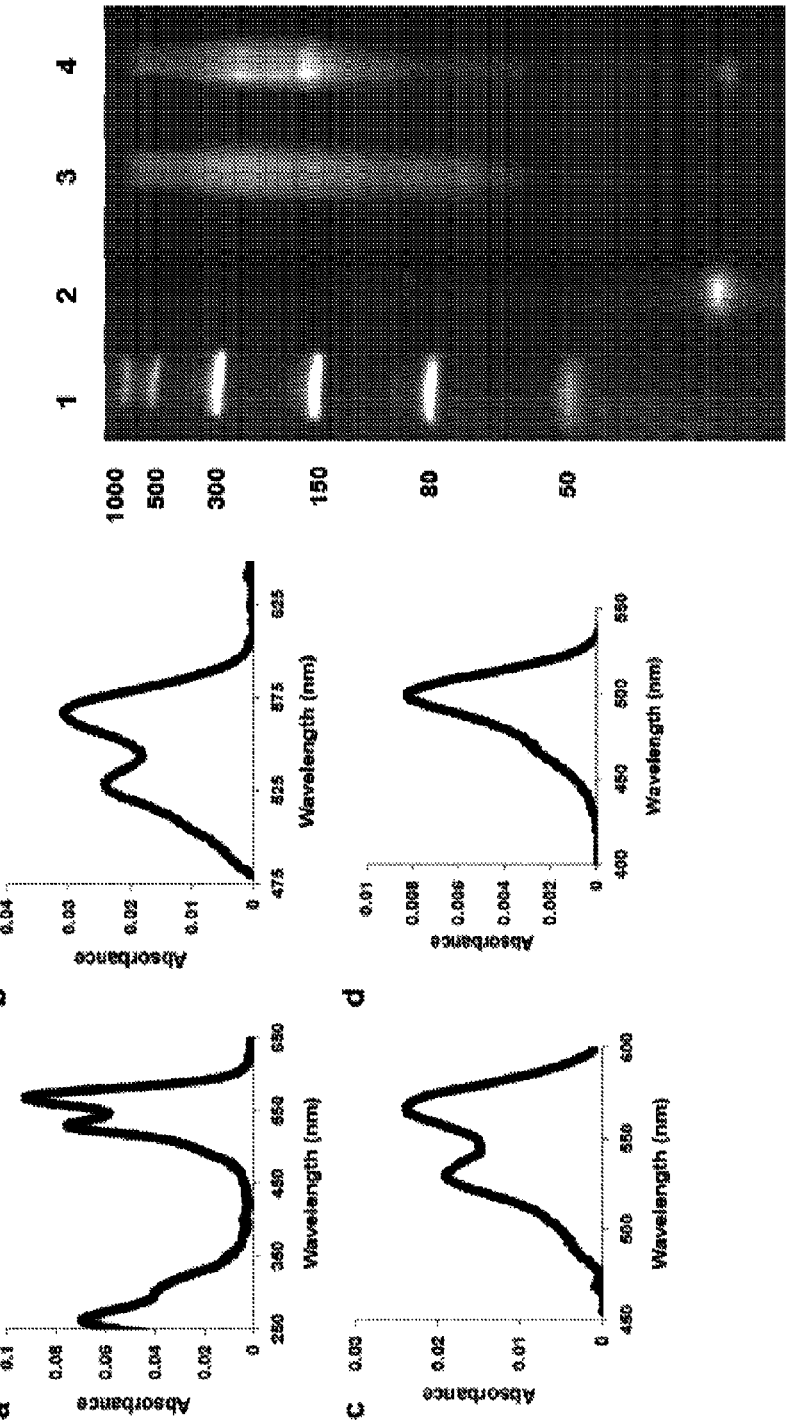
FIG. 20 is an ethidium bromide stained 15% TBE-UREA gel of the probes, where lane 1 is a low range ssRNA ladder; lane 2 is unconjugated oligonucleotides; lane 3 is PEG probe, and lane 4 is PEG-TAT probe.

The present invention may be understood more readily by reference to the following Detailed Description of the invention and the Examples included therein. Before the present compounds, compositions, and methods are disclosed and described, it is to be understood that this invention is not limited to any specific probes, specific targets, specific nucleic acid probes, specific nucleic acid targets, specific cell types, specific conditions, or specific methods, etc., as such may, of course, vary, and the numerous modifications and variations therein will be apparent to those skilled in the art. Throughout this description, various components can be identified as having specific values or parameters, however, these items are provided as exemplary embodiments. Indeed, the exemplary embodiments do not limit the various aspects and concepts of the present invention as many comparable parameters, sizes, ranges, and/or values can be implemented. The terms "first," "second," and the like, "primary," "secondary," and the like, do not denote any order, quantity, or importance, but rather are used to distinguish one element from another. Further, the terms "a," "an," and "the" do not denote a limitation of quantity, but rather denote the presence of "at least one" of the referenced item. Thus, for example, reference to "a nucleic acid probe" can mean that one or more than one nucleic acid probe can be utilized.

An aspect of the present invention includes a biomolecule probe comprising: a multivalent core comprising a plurality of attachment sites; a ligand having specificity for a target, wherein the ligand is bound to an attachment site of the multivalent core; and a reporter molecule, wherein the reporter molecule is bound to the ligand.

As used herein, the term "biomolecule" refers to many organic molecules that can be produced by a living organism or synthesized, including, but not limited to, proteins, peptides, polysaccharides, oligosaccharides, glycoproteins, lipids, phospholipids, polynucleotides, oligonucleotides, as well as small molecules such as primary metabolites, secondary metabolites, and other biological molecules that is capable of activating inhibiting or modulating a biochemical pathway or process.

The term "ligand" as used herein refers to a biomolecule or other chemical entity having a capacity or affinity for binding to a target. A ligand can include a protein or portion thereof, a peptide, a polysaccharide, an oligosaccharide, a sugar, a glycoprotein, a lipid, a phospholipid, a polynucleotide or portion thereof, an oligonucleotide, an aptamer, a nucleotide, a nucleoside, DNA, RNA, a DNA/RNA chimera, an antibody or fragment thereof, a nucleic acid-protein fusion, a hapten, a nucleic acid, and a virus or a portion thereof, as well as small molecules (e.g., a chemical compound) such as primary metabolites, secondary metabolites, and other biological molecules that is capable of activating inhibiting or modulating a biochemical pathway or process, and/or any other affinity agent, among others. A ligand can come from many sources, including libraries, such as the aptamer libraries, phage display libraries, or any other library as would be apparent to one of ordinary skill in the art after review of the disclosure of the present invention presented herein.

As used herein, a "target" or "target molecule" refers to a biomolecule that could be the focus of a therapeutic drug strategy or diagnostic assay or a combination thereof, sometimes referred to as a theranostic. Therefore, a target can include, without limitation, a protein or portion thereof, a peptide, a polysaccharide, an oligosaccharide, a sugar, a glycoprotein, a lipid, a phospholipid, a polynucleotide or portion thereof, an oligonucleotide, an aptamer, a nucleotide, a nucleoside, DNA, RNA, a DNA/RNA chimera, an antibody or fragment thereof, a nucleic acid-protein fusion, a hapten, a nucleic acid, and a virus or a portion thereof, as well as small molecules (e.g., a chemical compound) such as primary metabolites, secondary metabolites, and other biological molecules that is capable of activating inhibiting or modulating a biochemical pathway or process, and/or any other affinity agent, among others.

The ligand may be, for example, one member of a biointeractive complex that comprises two or more biomolecules that have a binding affinity for one another. Consequently, the target may also be one member of such a biointeractive complex that demonstrates binding affinity for the ligand. Examples of biointeractive complexes (e.g., ligand-target complexes) can include for example, a protein:protein complex, a protein:peptide complex, a polynucleotide:polynucleotide complex, a polynucleotide:oligonucleotide complex, an oligonucleotide:protein complex, a peptide:polynucleotide complex, an antibody:antigen complex, an enzyme:substrate complex, or a biomolecule:drug complex, among others.

The phrase "having specificity for a target" with respect of the ligand as used herein can also be referred to as the "binding activity" or "binding affinity" of the ligand relative to the target. These phrases may be used interchangeably herein and are meant to refer to the tendency of a ligand to bind or not to bind to a target. The energetics of these interactions are significant in "binding activity" and "binding affinity" because they define the necessary concentrations of interacting biomolecules, the rates at which these biomolecules are capable of associating, and the relative concentrations of bound and free biomolecules in a solution. The energetics are characterized through, among other ways, the determination of a dissociation constant, $K_d$. The specificity of the binding is defined in terms of the comparative dissociation constants ($K_d$) of the ligand for target as compared to the dissociation constant with respect to the ligand and other materials in the cellular environment or unrelated molecules in general. Typically, the $K_d$ for the ligand with respect to the target will be 2-fold, preferably 5-fold, more preferably 10-fold less than $K_d$ with respect to target and the unrelated material or accompanying material in the cellular environment. Even more preferably, the $K_d$ will be 50-fold less, more preferably 100-fold less, and more preferably 200-fold less than $K_d$ with respect to target and the unrelated material or accompanying material in the cellular environment.

In the various embodiments of the present invention, the ligand is bound to a multivalent core comprising a plurality of attachment points. As used herein, the term "plurality" refers to more than one. As a result, a multivalent core comprises more than one attachment sites that have the capacity to bind a ligand. The core can be made of many materials, including, but not limited to poly(ethylene)glycol and derivatives thereof or avidin and derivatives thereof.

For example, a core comprising poly(ethylene)glycol can have a molecular weight ranging from about 5 kilodaltons to about 50 kilodaltons. More preferably, the poly(ethylene) glycol can have a molecular weight ranging from about 5 kilodaltons to about 30 kilodaltons, and even more preferably about 20 kilodaltons. The poly(ethylene)glycol can be a multi-arm poly(ethylene)glycol, having two arms, four arms, six arms, or eight arms. Each arm represents an attachment site on the multivalent core.

In another example, a core can comprise avidin or a derivative thereof, such as streptavidin, NeutrAvidin and CaptAvidin, among others. Avidin or derivatives thereof demonstrate a strong affinity for biotin and are generally capable of binding four biotins per molecule (i.e., tetravalent).

Regardless of the type of cores, in some embodiments of the present invention, all of the attachment sites of the multivalent core are bound to a ligand. In such embodiments, the ratio of ligand to attachment sites on the multivalent core is equal to about 1. In other embodiments of the present invention, only a portion of the attachment sites of the multivalent core are bound to a ligand or a ligand may be bound to multiple attachment sites. Consequently, ratio of ligands to attachment sites may be less than about 1. Further, on a given multivalent core, one or more types of ligand may be bound to the multivalent core.

In the various embodiments of the present invention, the ligand is also bound to a reporter molecule. As used herein, a "reporter molecule" is a detectable compound or composition that is conjugated directly or indirectly to another molecule (such as the ligand or multivalent core) to facilitate detection of that molecule. Specific, non-limiting examples of reporter molecules include fluorescent and fluorogenic moieties, enzymatic moieties, haptens, affinity tags, and radioactive isotopes. The reporter molecule can be directly detectable (e.g., optically detectable) or indirectly detectable (for example, via interaction with one or more additional molecules that are in turn detectable). A ligand may be labeled with one or more reporter molecules. Thus, the ratio of reporter molecules to ligands may be greater than or equal to about 1.

Exemplary reporter molecules in the context of the probes disclosed herein are fluorophores. Numerous fluorochromes are known to those of skill in the art, and can be selected, for example from Invitrogen, e.g., see, The Handbook—A Guide to Fluorescent Probes and Labeling Technologies, Invitrogen Detection Technologies, Molecular Probes, Eugene, Oreg.). Examples of particular fluorophores that can be attached (for example, chemically conjugated) to a FPC nucleic acid molecule are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, ATTO dyes, Brilliant Yellow, coumarin and derivatives such as coumarin, 7-amino-4-methylcoumarin (AMC, Coumarin 120), 7-amino-4-trifluoromethylcouluarin (Coumaran 151); cyanines; cyanosine; 4',6-diaminidino-2-phenylindole (DAPI); 5',5''-dibromopyrogallol-sulfonephthalein (Bromopyrogallol Red); 7-diethyl amino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC(XRITC); IR dyes, 2',7'-difluorofluorescein (OREGON GREEN); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacro Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N, N',N'-tetramethyl-6-carboxyrhodamine (TAMRA); tetramethyl rhodamine; tetramethyl rhodamine isothiocyanate (TRITC); riboflavin; rosolic acid and terbium chelate derivatives as well as other photostable dyes known in the art.

An exemplary embodiment of the present invention includes a ribonucleic acid (RNA) imaging probe. As the name implies, the probe can be utilized to visualize the presence of various types of RNA in cell, including, but not limited to messenger RNA (mRNA), transfer RNA (tRNA), ribosomal RNA (rRNA), transfer-messenger RNA (tmRNA), microRNA (miRNA), small interfering RNA (siRNA), small nuclear RNA (snRNA), small nucleolar RNA (snoRNA), and viral genomes comprising RNA and RNA-based intermediates thereof, among others.

In an exemplary embodiment, the RNA imaging probe includes an oligonucleotide as the ligand. As used herein, an "oligonucleotide" refers to a plurality of nucleic acids having a sequence sufficient to hybridize to at least a portion of a target nucleic acid, such as a target RNA. As used herein, the term "nucleic acid" is intended to include DNA molecules (e.g., cDNA or genomic DNA) and RNA molecules, as described above, and analogs of the DNA or RNA generated using nucleotide analogs. As referred to herein, nucleic acids that are "complementary" can be perfectly or imperfectly complementary, as long as the desired property resulting from the complementarity is not lost, e.g., ability to hybridize to the target nucleic acid.

The oligonucleotide sequence can demonstrate substantial complementarity to the target nucleic acid sequence. As used herein, the term "substantial complementarity" to the target nucleic acid sequence means that a oligonucleotide includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, 99%, or 100% sequence complementarity to the target nucleic acid sequence.

The nucleic acids of the present invention may be substantially isolated or alternatively unpurified. An "isolated" or "purified" nucleic acid is one that is substantially separated from other nucleic acid molecules that are present in the source of the nucleic acid. Preferably, an "isolated" nucleic acid is substantially free of sequences that naturally flank the nucleic acid (i.e., sequences located at the 5' and 3' ends of the nucleic acid). Moreover, an "isolated" nucleic acid molecule can be substantially free of other cellular material, or culture medium when produced by recombinant techniques, or chemical precursors or other chemicals when chemically synthesized. The oligonucleotide ligand typically comprises substantially purified nucleic acid.

The nucleic acid probes of the invention can be DNA, RNA or a chimeric mixture of DNA and RNA, or derivatives or modified versions of DNA or RNA, so long as the oligonucleotide is capable of hybridizing to the desired target nucleic acid. For example, an oligonucleotide probe of the present invention can be chemically synthesized using naturally occurring nucleotides or variously modified nucleotides designed to increase the biological stability of the molecules or to increase the physical stability of the duplex formed between the complimentary nucleic acids (i.e., the ligand and target). A preferred example of a class of modified nucleotides which can be used to generate the nucleic acid probes is a 2'-O-methyl nucleotide. Additional examples of modified nucleotides which can be used to generate the nucleic acid probes include, but are not limited to, 5' thiol modified 2'-O-methyl uridine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3), 2,6-diaminopurine, and locked nucleic acids.

The oligonucleotide comprises three regions: a hybridization region, a spacer region, and an attachment region. In an exemplary embodiment, the oligonucleotide comprises, in a 5' to 3' direction, an attachment region, a spacer region, and a hybridization region.

The hybridization region of the oligonucleotide probe typically comprises a region of nucleotide sequence that hybridizes to at least about 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 consecutive nucleotides of a target nucleic acid. In an exemplary embodiment, the hybridization region comprises about 10 to about 20 2'-O-Methyl nucleotides, wherein the hybridization region has an average G/C content of about 50%. The hybridization region can have complementarity to any target RNA of interest, for example a cellular RNA associated with a biochemical or signaling pathway, a cellular RNA associated with specific disease or condition, a viral RNA, a bacterial RNA, a RNA associated with an inherited disease, or a RNA associated with cancer, among others.

The spacer region of the oligonucleotide operates to spatially separate the hybridization region from the multivalent core. Although not wishing to be bound by any particular theory, the hybridization efficiency of the RNA imaging probe can be increased by spacing away the hybridization region from the surface of the multivalent core making the hybridization region more accessible for hybridization with its target. The sequence and length of the spacer region can be determined empirically; however, it has been found that a spacer region having a sequence comprising a plurality of thymine bases, adenine bases, or combinations thereof provide sufficient spacing. Experimental data indicates that thymidines, adenosines, or combinations thereof are particularly effective spacer regions. In an exemplary embodiment, the spacer regions comprises about 5 to about 10 nucleotides, and more preferably about 6 to about 7 nucleotides.

The hybridization region and the spacer region can also comprise nucleotide derivatives suitable for conjugation of a reporter molecule. In an exemplary embodiment, the oligonucleotide can contain about 2 to about 8 nucleotide derivatives suitable for conjugation to a reporter molecule, and preferably about 3 to about 4 nucleotide derivatives. Such nucleotides may be located only in the hybridization region, only in the spacer region, or in both the hybridization region and the spacer region. In one example, amine-modified thymidines can be located in both the hybridization and spacer regions for conjugation of the oligonucleotide to NHS-ester fluorophores, such as Atto 488, Cy3B, or Atto 647N. Of course, one of ordinary skill in the art could determine the appropriate nucleotide derivative and number thereof to conjugate different reporter molecules of fluorophores and to tune the sensitivity of the probe, respectively.

Selection of an attachment region for the oligonucleotide depends largely upon the type of multivalent core to which the oligonucleotide will be attached. For example, in the context of an avidin-based core, the attachment region can comprise a 5' biotin modification to the oligonucleotide. Alternatively, in the context of a poly(ethylene)glycol-based core, the attachment region can comprise a 5' thiol modified 2'-O-methyl uridine residue.

In addition to the ligands (e.g., oligonucleotides) described above, the probes of the present invention can further comprise a targeting moiety or an epitope moiety. As used herein, the term "targeting moiety" refers to a substance associated with the multivalent core that enhances binding, transport, accumulation, residence time, bioavailability, or modifies biological activity of the probe. The targeting moiety can include, but is not limited to, an organic or inorganic molecule, a peptide, a peptide mimetic, a protein, an antibody or fragment thereof, a growth factor, an enzyme, a lectin, an antigen or immunogen, a virus or component thereof, a receptor, a receptor ligand, a toxin, a polynucleotide, an oligonucleotide or aptamer, a nucleotide, a carbohydrate, a sugar, a lipid, a glycolipid, a nucleoprotein, a glycoprotein, a lipoprotein, a steroid, a hormone, a chemoattractant, a cytokine, a chemokine, or a drug, among others.

The term epitope moiety, as used herein, refers to any structure, sequence, or antigenic determinant that is recognized by an antibody. Examples of suitable epitope moieties include, but are not limited to, a FLAG-tag, a HA tag, a c-myc tag, a polyhistidine tag, green fluorescent protein (GFP), digoxigenin, an α-tubulin tag, a B-tag, an E tag, a herpes simplex virus gD tag, a Pk-tag, a protein C tag, a T7 tag, a vesicular stomatitis virus glycoprotein tag, biotin, or a glutathione-S-transferase tag.

Another aspect of the present invention comprises a method for detecting a single molecule of RNA using the RNA imaging probe described above. Such a method comprises delivering an effective amount of an RNA imaging probe to a cell and detecting a molecule of a RNA in a cell. As used herein, the term "cell" refers to all eukaryotic and prokaryotic cells, as well as unicellular organism and multicellular organisms or cells or tissues derived therefrom. Indeed, the word cell can encompass both living cells and fixed cells.

The delivery of the probe can be accomplished by many methods known in the art. Although not wishing to be bound by any particular theory, it is currently believed that the delivery of probes to a cell should generally avoid the endocytic pathway, so as to avoid the accumulation of probes in endosomal compartments. The probes of the present invention can be delivered to cells through transfection methods; however, transfection is a generally inefficient process. Thus, preferred methods of delivery of the probe to a cell include microinjection, TAT-mediated transduction, or reversible cell permeabilization, such as through the use of streptolysin 0.

The phrase "effective amount" as used herein is an amount of a probe that produces a desired effect in a cell, such as detecting a molecule of a RNA in a cell. This amount (i.e., dosage) may vary depending upon a number of factors, including, but not limited to, the characteristics of the probe (including activity, pharmacokinetics, pharmacodynamics, and bioavailability) and cell type, among others. One skilled in the art will be able to determine an effective amount through routine experimentation, namely by monitoring the cellular response to administration of a probe and adjusting the dosage accordingly. Typically, fluorescent probes, such as molecular beacons, require relatively high doses to detect RNA, such as 1 µM to 2 µM. One particular advantage of the probes of the present invention is that these probes can be delivered at relatively low concentrations (less than 1 µM) and can detect single molecules of RNA. The probes of the present invention can be delivered in nanomolar concentrations, such as about 1 nM to about 100 nM, and more preferably between about 5 nM to about 30 nM.

Detecting a molecule of a RNA in a cell can involve many mechanisms of detection of nucleic acids know in the art. In an exemplary embodiment, detection of a molecule of RNA includes visualizing the association of the RNA imaging probe with the molecule of a RNA in a cell through many modes of microscopy, for example confocal microscopy or epifluorescent microscopy. Through the use of the probes and microscopy, it is possible to visualize and monitor the trafficking of a target RNA through a cell. Detection of a molecule of RNA can also be performed by affinity chromatography, such as through immunoprecipitation. By using affinity chromatography methods, such as immunoprecipitation and the like, not only can the target RNA molecule be detected, but additional biomolecules (e.g., RNA, proteins, etc.) that are associated with the target RNA can also be detected and/or identified. Thus, the compositions and methods of the present invention provide a valuable tool for the identification of the interactome associated with a target RNA.

Another particular advantage of the probes of the present invention is that they can be used to monitor native, non-engineered RNA in a cell. A "native, non-engineered RNA" is an RNA that is not introduced into a cell through a plasmid or an RNA that has a sequence that has non-native sequences or additional sequences not normally present in the RNA. Although plasmid expressed RNAs could be studied using the probes of the present invention, the expression of plasmid-derived RNA is not preferable as they alter the biology of RNA expression, translational efficiency, decay, and stability. The probes of the present invention overcome the shortcomings associated with plasmid-expressed RNAs and these probes can be used to detect endogenous cellular RNAs with single molecule sensitivity. The probes of the present invention can also be used to visualize exogenous RNA, such as that derived from various microorganisms, such as bacteria, viruses, and fungi.

It should be understood, of course, that the foregoing relates only to exemplary embodiments of the present invention and that numerous modifications or alterations may be made therein without departing from the spirit and the scope of the invention as set forth in this disclosure. Therefore, while embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

It should be noted that all patents, patent applications, and references included herein are specifically incorporated by reference in their entireties.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

Example 1

Single Molecule-Sensitive Probes for Imaging RNA in Live Cells

The below Example was published in *Nature Methods*, Vol. 6, No. 5, (May 2009). Consequently the referenced Figures can be viewed in color in this publication, which is hereby incorporated by reference.

Materials and Methods.

MTRIPs.

The 2' O-methyl RNA-DNA chimera nucleic acid ligands were synthesized by Biosearch Technologies, Inc. Each contains a 5' biotin modification and multiple dT-C6-NH2, modifications. The streptavidin used for the core was purchased from Pierce. Probes were assembled by first labeling the free amine groups on the ligands with either Cy3B-NHS ester (GE Healthcare) or Atto 647N-NHS ester (Atto-Tec GmbH) using manufacturers' protocols. Free dye was removed using both Nanosep spin columns (Pall Corp.) and illustra G-25 size-exclusion columns (GE Healthcare). The purified ligands were resuspended in 1× phosphate-buffered saline (PBS; pH 7.4) and mixed at a 10:1 molar ratio with streptavidin for 1 h at room temperature (18-22° C.). Free ligands were removed using 30 kDa Nanosep spin columns, and stored at 1 mM final concentration in 1×PBS at 4° C. When multiple probes were used, each probe was completely assembled and filtered separately, and then mixed with equimolar concentrations in streptolysin O and medium just before delivery into cells.

Cells and Virus.

A549 lung carcinoma cells (American Type Culture Collection CCL-185) were grown in DMEM (Sigma Aldrich) with 10% fetal bovine serum (FBS; Hyclone) with 100 U ml$^{-1}$ of penicillin and 100 mg ml$^{-1}$ of streptomycin. Virus used was the A2 strain of hRSV (American Type Culture Collection VR-1544) at a titer of 1×10$^6$ 50% tissue culture infectious dose (TCID$_{50}$) ml$^{-1}$. The titer was evaluated by serial dilution and immunostaining, 4 d after infection. Infection data shown (FIG. 3 and FIGS. 8-10) was at day 1 after infection and with a multiplicity of infection of 5. All cells were infected at greater than 80% confluence, by removing the media, washing with 1×PBS (without Ca$^{2+}$ and Mg$^{2+}$) and then adding virus to the cells for 30 mM at 371 C. After the 30-mM incubation, complete medium was added. For the motile epithelial cell experiments, A549 cells were seeded at 5% confluence such that there were a substantial number of cells without contacts with other cells. For the motile fibroblast experiments, primary chicken embryonic fibroblasts (Charles River Laboratories) were grown in CEF growth medium (Charles River Laboratories), containing 5% FBS and seeded at 5% confluence.

Probe Delivery.

MTRIPs were delivered into A549 and CEF cells using a reversible permeabilization method with streptolysin O (Sigma). Cells grown in complete medium were first washed with 1×PBS and then incubated with a mixture of 0.2 U ml$^{-1}$ of streptolysin O and probe in an appropriate amount of complete growth medium for 10 mM at 37° C. The mixture of streptolysin O, probe and medium was then removed and replaced with fresh, complete growth medium or Leibovitz's L15 medium supplemented with 10% FBS. Live cells were imaged typically 20 min immediately after delivery by epifluorescence microscopy. Using streptolysin O-based delivery, probes were delivered into A549 and CEF cells with 100% efficiency.

Counting Granules and Statistical Analysis of RNA Granule Populations.

For data shown in FIG. 2 and FIG. 10, granules were identified and counted using Improvision's Volocity software in three dimensions using either confocal images or from widefield fluorescence images, deconvolved using an iterative deconvolution algorithm in Volocity. For data shown in FIG. 2, granules were counted using deconvolved data and identified based on the s.d. of intensities; 4 s.d. above the mean was used to locate the granules in all cases because it avoided the detection of noise or objects substantially smaller than the point spread function. Because of this, no limit on minimum granule size was necessary when counting granules. In general, the cells deconvolved using the three-dimensional interative algorithm in Volocity lacked considerable noise due to filtering in the algorithm. Notably, the s.d. in mean granule intensity for the granules in FIG. 2$c$ and in the serum-starved cell (data not shown) were only 25% and 21%, respectively, reflecting the uniformity of the granules when measured in three dimensions. For data shown in FIG. 10, the number of granules was detected using the same criteria using confocal data from tetravalent MTRIPs and a monovalent ligand (ligands not connected by streptavidin) in approximately 30 cells each. The results were compared using the Wilcoxon-Mann-Whitney (WMW) test to determine whether the two samples came from the same population. WMW is a nonparametric test is traditionally used to test equality of locations in two populations, but in its general form this test is about the equality of distributions. The null hypothesis states that the distributions of the two samples coincide and the alternative is that the distributions differ. The P value for WMW test when comparing the number of granules detected by each probe was 0.8737, which means that the evidence for the null hypothesis is decisive; consequently, the distributions were assumed to be the same.

Plasmids and Transfections.

The pSRa-GFP-HA-TIA-1 plasmid was used to image stress granules in living cells. A549 cells plated in penicillin- and streptomycin-free medium were transfected using Fugene HD (Roche) at a ratio of Fugene HD to DNA of 2.5 ml mg$^{-1}$.

Time-Lapse Fluorescence Microscopy.

Live-cell video microscopy was performed using cells grown in Bioptechs T4 plates with an objective heater. The cells were imaged in Leibovitz's L15 medium supplemented with 10% FBS. Images were taken with a Zeiss Axiovert 200M microscope, with an X63, numerical aperture (NA) =1.4 Plan-Apochromat objective and Hamamatsu ORCA-ER AG camera, using Chroma 49002 ET-GFP and 49004 ET-Cy3 filter sets, controlled by Volocity software. For β-actin mRNA granule dynamics, images were taken either at 1 or 5 Hz with 90-ms exposures for 3 mM and 30 s, respectively. For the stress granule-RNA experiments, images of GFP-TIA-1 and the Cy3B-labeled MTRIPS were taken at 0.2 Hz (every 5 s), with exposure times of 71 and 41 ms, respectively, for up to 8 min. Stress granule-RNA time-lapse microscopy. A549 cells, transfected with the above plasmid for 24 h were then infected with hRSV as above. Twenty-four hours after infection, the MTRIPs were delivered at 25 nM final concentration, and the cells exposed to 1.0 mM sodium arsenite for 30 min. During the 30-min incubation, the cells were observed periodically using epifluorescence microscopy. After 15 mM of exposure, stress granules (marked by GFP-TIA-1 aggregates) were observed; an imaging plane containing both RNA granules and stress granules was chosen and time-lapse microscopy was initiated. Out-of-focus light was removed using Volocity's 2D deconvolution algorithm.

Starvation Assay.

A549 cells were serum-starved in DMEM with 100 U ml$^{-1}$ of penicillin and 100 mg ml$^{-1}$ of streptomycin for 48 h. MTRIPs (human (β-actin mRNA probes 1 and 2) were delivered with streptolysin O. Twenty minutes after delivery, the cells were fixed in 4% paraformaldehyde and stained with DAPI. The granules in a particular cell were then counted using the method described above.

Immunostaining.

Twenty to thirty minutes after probe delivery, cells were fixed in 4% paraformaldehyde in 1×PBS for 10 mM at room temperature. After fixation, cells were permeabilized using 0.2% Triton-X 100 for 5 mM at room temperature, washed in 1×PBS, blocked for 30 mM in 5% BSA (ultrapure), washed in 1×PBS, incubated with primary antibody for 30 mM at 37° C., washed 3× with 1×PBS, incubated in secondary antibody labeled with Alexa 488 for 30 min at 37° C., washed 3× with 1×PBS, labeled with DAPI for 5 min (in the RSV experiments) and then mounted in PVA with Dabco. The monoclonal antibody for the hRSV nucleocapsid protein was from Abcam, and the polyclonal Ab for ZBP1 from the Bassett laboratory. Polyclonal ZBP1 antibodies were produced by immunizing guinea pigs with a synthetic peptide corresponding to residues 162-175 (SEQ ID NO 1: CGPENGRRGGFG-SRG; the first Cys is for conjugation) within a hinge region between two RRM and four KH domains of human ZBP1. This region is conserved completely among mouse, rat and human ZBP1 proteins, but not Imp2 or Imp3 The ZBP1 antibody does not recognize mouse Imp2 or Imp3 by western blotting (data not shown). F-actin was stained using Alexa 488-labeled phalloidin (Invitrogen).

Fluorescence Imaging.

Immobilized Cy3B and Atto 647N probes on the glass surface were imaged using a Zeiss Axiovert 200M microscope with an X63, NA=1.4 Plan-Apochromat objective, using Chroma 49004 ET-Cy3 and 49006 ET-Cy5 filter sets, with 500-ms exposures. An EXFO excite 120 light source with a ND (neutral density) ¼ 0.4 (40% transmission) was used for fluorescence excitation, and a Hamamatsu ORCA-ER AG for taking digital images. Live-cell images of single probes within A549 cells were taken with 350 ms exposures under the same illumination conditions. Z-dimension stacks were taken in both cases, in 200-nm steps, and deconvolved using Volocity iterative deconvolution algorithm. Cells used in the human β-actin mRNA scrambled probe experiments were fixed after live-cell hybridization and imaged similarly to the immobilized probes, but with 200-ms exposures and deconvolved in Volocity. Time-lapse live cell images were taken as discussed above, and were processed with Volocity's 2D or fast deconvolution algorithm. In the stress granule control experiments, live cell images were taken similarly to the single probe images but with 50-ms exposures. hRSV after delivery, fixed-cell control experiments were imaged with a ZeissLSM 510 Meta using an X63, NA=1.4, Plan-Apochromat objective. All images were taken using multi-track scanning for each fluorophore to prevent bleed-through. Z-dimension stacks were taken in 0.5-mm increments; the 543 nm laser (Cy3B probe) was set at 25% power, the 488 nm laser (for N protein immunostaining) was set at 37%, and the pinholes were set to an airy unit of 1 (equal to airy disk). β-actin mRNA, actin-related protein 2 homolog mRNA and ZBP1, in the chicken embryonic fibroblasts, were imaged under similar conditions to the human β-actin mRNA experiments.

Image Analysis.

Images were analyzed using Volocity software and NIH ImageJ. Volocity was used to deconvolve the widefield images (2D and full-iterative), reconstruct the images in three dimensions, identify individual probes based on intensity and measure the mean intensity within granules of all sizes. It was also used to perform the three-dimensional co-localization calculations of Manders coefficient. The Color Profiler tool in ImageJ was used to obtain profile data for the intensity plots from the merged images.

Live-Dead Assay.

To assess the effects of streptolysin O, and the Invitrogen L-3224 Live/Dead Viability/Cytotoxicity kit for mammalian cells was used as per the manufacturer's instructions. The images were taken on a Zeiss 200M widefield epifluorescence microscope with an LD Plan-Neofluar ×20, NA=0.4 objective, Hamamatsu ORCA ER-AG camera, and appropriate filter sets.

EXPERIMENTAL RESULTS

Currently researchers use a vast excess of probes or plasmid-derived RNA to image RNA with single-molecule sensitivity. Either both the RNA and probe are expressed from a plasmid, requiring binding of up to 48 MS2-GFP molecules, or just the RNA is expressed from a plasmid, requiring binding sites for 96 molecular beacon probes to achieve single-molecule sensitivity. As plasmid-derived RNA restricts usage to cell types that can be efficiently transfected and is susceptible to artifacts caused by overexpression, imaging native RNA is preferred, but requires a more sensitive probe to achieve single-molecule sensitivity with a limited number of bound probes. Multiply labeled tetravalent RNA imaging probes (MTRIPs) were designed composed of a 2'-O-methyl RNA-DNA chimera nucleic acid ligand with four or five amino-modified thymidines, 5' biotin modification and a short (5-7-base) poly(T) sequence to extend the ligands from the surface of streptavidin. The amino-modified thymidines were used to conjugate N-hydroxysuccinimide (NHS) ester-modified fluorophores to the ligand. On average, each ligand was labeled with three fluorophores, limiting self-quenching. Fluorophores were chosen with quantum yields above 65% and they exhibited little triplet state excitation. The multiply labeled monovalent ligands were tetramerized via their binding to streptavidin, which increased probe brightness fourfold (FIG. 1a). MTRIPs, when delivered via reversible cell membrane permeabilization with streptolysin O (FIG. 1b), allowed for single RNA molecule sensitivity using conventional fluorescence microscopy techniques. The target RNA was identified by the enhanced signal-to-background ratio achieved through the binding of multiple MTRIPs per RNA (two or three), via Watson-Crick base pairing, or if using a single MTRIP per RNA, through the natural localization of RNA (FIG. 1c). This is analogous to the MS2-GFP binding systems, but uses native target sequences and fewer binding sites.

To characterize probe sensitivity and delivery to the cytosol, probes targeting the genomic RNA of the wild-type strain A2 of human respiratory syncytial virus (hRSV) were immobilized on glass surfaces and delivered them into non-infected A549 cells using streptolysin O. More specifically, probes at 2 nM concentrations were immobilized on a glass surface by adding them in growth media to a coverslip well and incubating them for 10 minutes at 37° C. The mixture was removed, growth medium was added, and the glass surface was imaged. Individual batches of each probe (see FIG. 4a), in addition to a mixture of Cy3B and ATTO 647N labeled probes (see inset image FIG. 4a), were imaged on the glass surface. Individual probes were identified, and the mean intensity within the diffraction limited spots was plotted as a histogram (FIG. 4b). After examining the images of the probe mixtures on glass, the histograms of mean probe intensity and three-dimensional plots of the intensity of individual probes on the glass surface, we concluded that the images detected single probes and not aggregates (Table 1 and FIG. 4). If the probes were aggregating, the histograms would show non-unimodal behavior and mixtures of different color probes would co-localize, which was not the case. In addition, hRSV targeting probes labeled with Cy3B (GE Healthcare) and Atto 647N (Atto-Tec GmbH) were delivered into non-infected A549 cells. From a single optical plane within the live cell, individual probes were observed as being homogenously distributed in the cytoplasm (FIG. 1d-e) and localization or accumulation of probes was not observed.

TABLE 1

| SEQ ID NO | RNA Target | Ligand | Accession Number & Location within Gene |
|---|---|---|---|
| SEQ ID NO 2 | hRSV genomic RNA | 5'-biotin-UXTXTTXAAAAAXGGGGCAAAXAA-3' | M74568; 39-55; 590-606; 2323-2339 |
| | Human β-actin mRNA | | NM_001101.2 |
| SEQ ID NO 3 | Probe 1 | 5'-biotin-UXTTTXAXAGCACAGCCXGGAXA-3' | 494-478 |
| SEQ ID NO 4 | Probe 2 | 5'-biotin-TTTTTTXAUUXCCCGCXCGGCCGXG-3' | 696-679 |
| | Chicken β-actin mRNA | | |

TABLE 1-continued

| SEQ ID NO | RNA Target | Ligand | Accession Number & Location within Gene |
|---|---|---|---|
| SEQ ID NO 5 | Probe 1 | 5'-biotin-TTTTTGGAGXAACGCGGXCAGXCAG-3' | 57-38 (61-38 Tyagi, 2004) |
| SEQ ID NO 6 | Probe 2 | 5'-biotin-TTXTTTCAAXAUCAXCAUCCAXGGC-3' | 84-66 (83-66 Tyagi, 2004) |
| SEQ ID NO 7 | Probe 3 | 5'-biotin-TTTTTXAGGAXACCXCUUXUGCUCXGG-3' | 262-242 (262-240 Tyagi, 2004) |
|  | Chicken arp2 mRNA |  | NM_205224 |
| SEQ ID NO 8 | Probe 1 | 5'-biotin-TTTTXTTUCCXCCCCAGCGXGUCCA-3' | 130-112 |
| SEQ ID NO 9 | Probe 2 | 5'-biotin-TTTTTXACCAAGCXTCXCCAGCACAC-3' | 1280-1261 |
| SEQ ID NO 10 | Probe 3 | 5'-biotin-TTTXTTCAGXUGAXCUTAXAAUAGG-3' | 243-225 |
| SEQ ID NO 11 | Scrambled Probe | 5'-biotin-TTTTTTTXCUAAXACXGUAXCAUCXGC-3' |  |

Boldface: 2'-O-Methyl RNA; X: dt-C6-NH2; all others are DNA; underline: hybridization region To test the ability to image single RNAs, two Cy3B-labeled MTRIPs designed to target two regions of the human β-actin mRNA coding sequence (human β-actin mRNA probes 1 and 2; Table 1) and an Atto 647N-labeled 'scrambled' probe (no target in human genome) (30 nM each) were simultaneously delivered using streptolysin O into A549 cells. Twenty minutes after delivery, the cells were fixed in 4% paraformaldehyde and subsequently imaged. Individual RNAs could be imaged in both fixed and live cells, but the cells were fixed for quantification because of the dynamic nature of RNA granules. For β-actin, individual 'unbound' probes were observed as well as localized granules with twice the intensity (FIG. 2a-c). β-actin mRNA was prevalent in the perinuclear region of the cell and also localized to the leading edges, whereas the 'scrambled' probe produced perinuclear signals and localized not at the cell periphery but in the cytoplasm, demonstrating β-actin probe specificity. Localization was quantified in an intensity profile of the confocal image (FIG. 2b). From the lower-noise, widefield-deconvolved image (FIG. 2c), the average single-probe intensities, quantified from probes on the glass surface, were removed via thresholding, and the remaining granules were counted using Volocity (Improvision) software. Using this approach, single β-actin mRNAs, containing approximately twice the single probe intensity, were observed in the cell (FIG. 2c) and a total of 1,455 granules was detected. Granule mean fluorescence intensity (calculated from the three-dimensional reconstruction) had a measured s.d. of only 25% of the mean, reflecting the uniformity of the granules when measured in three dimensions. The granule count was consistent with previous quantifications (1,500 in serum-stimulated cells), using a similar analysis for β-actin mRNA in epithelial cells. In addition, β-actin mRNA granules were imaged in living cells by time-lapse widefield fluorescence microscopy (FIG. 2d). Images were collected with 90-ms exposure times at both 1 Hz and 5 Hz for 3 min and 30 s, respectively. This demonstrated the capacity to use this method in low and high-speed tracking experiments; similar particle trajectories have been demonstrated for plasmid-derived mRNAs. As an additional control, A549 cells were serum starved for 48 h, and the β-actin mRNA granules in cells fixed after live-cell hybridization were counted. A representative cell contained only 409 granules as compared with 1,455 granules detected in a cell grown with serum (data not shown), consistent with previous experiments. We also performed single-probe imaging of clustered RNAs and co-localized them with β-actin mRNA binding protein, ZBP1 in three dimensions (FIGS. 5 and 6), and simultaneously imaged β-actin mRNA, actin-related protein 2 homolog mRNA and ZBP1 protein, in primary chicken embryonic fibroblasts (FIG. 7).

Further evidence that these probes can be used to image native RNA was provided by targeting human β-actin mRNA in motile A549 cells. In this case, when targeting β-actin mRNA only one site, previously identified, was used (see Table 1). β-actin mRNA, in motile cells, has been described to colocalize with the RNA binding protein, ZBP12 and with F-actin. Delivering MTRIPs at 30 nM and 1 nM concentrations, those associations were easily observed in cells fixed post live-cell hybridization and stained with an anti-ZBP1 antibody. In FIG. 5a-b outstretched pseudopods showed colocalization in both the image and in the intensity profile plot, while in FIG. 5c-d, MTRIPs were observed aligned with stained stress fibers (see merge as well as inset image). From the widefield deconvolved 2D images, 3D images were reconstructed in Improvision's Volocity software (FIG. 6a). From the overlap of voxels generated in Volocity, the Manders overlap coefficient was calculated as 0.92, (FIG. 6b) clearly indicating colocalization in three dimensions between human β-actin mRNA detected with MTRIPs and ZBP1.

In order to show the flexibility and applicability of this method, simultaneous imaging of two mRNAs in primary chicken embryonic fibroblasts (CEF) was performed (FIG. 7). CEFs were used because they have been a well-studied model system for studying RNA localization. Three MTRIPS targeting separate sequences on β-actin mRNA and arp2 mRNA were chosen based on both previous sequences used 4 and mFOLD folding of arp2 mRNA, where large single stranded loop sections were chosen. Even though only 2 probes per RNA are necessary for specific detection in non-clustered RNA (see FIG. 2), in order to optimize the signal for future dynamics studies, three probes per RNA were utilized (Table 1). β-actin targeted MTRIPs were labeled with ATTO 647N and arp2 targeted probes with Cy3B. Probes were delivered into CEFs (30 nM for each probe) for 10 minutes via SLO permeabilization; twenty minutes after delivery one set of cells was fixed for ZBP1 immunostaining while the other set utilized for live-cell imaging. In FIG. 7a an extended view image of arp2 (red) and β-actin (blue) mRNA, and ZBP1 (green) in a motile primary CEF is presented. Intensity profiles (FIG. 7a-b) through two cross-sections of the extended view demonstrate two types of localization; in the perinuclear region, β-actin mRNA signal is not correlated with the arp2 mRNA signal, especially from approximately pixel 100 to 225 in profile 1 and from 100 to 150 and 175 to 225 in profile 2; ZBP1 and β-actin mRNA are correlated within these same regions. While, from a single plane image (FIG. 7c-f) of the cell near the glass surface, (FIG. 7c-d); colocalization of arp2 (red) and β-actin (blue) mRNA, and ZBP1 (green) can be observed within the lamellipodium, especially at the leading edge. Similar colocalization of the RNAs was observed in the live-cell image within a cellular protrusion and along the cellular periphery; this was demonstrated quantitatively in the intensity profiles (FIG. 7g-h). In addition, in order to demonstrate that SLO delivery does not significantly affect even primary cells, phase contrast images of representative cells before and after SLO exposure (FIG. 7i), show no changes in cell morphology or their ability to create lamellipodia, necessary for motility.

The localization of both mRNA within the lamellipodia shown here, is consistent with a previous report on their localization; our data though suggests that the two mRNA are likely separate within the perinuclear region but are packaged together when transported to protrusions or lamellipodia. This is reasonable given a report that arp3 mRNA likely contain a ZBP1 binding site, and from our own sequence alignments (data not shown), arp2 mRNA are also likely to contain one. From the one previous report5, they claim these mRNA localize but do not colocalize, but from our examination of their data (data not shown), they may have underestimated the amount of colocalization.

To test the utility of these probes for the study of RNA-protein colocalization in live cells, Cy3B-labeled MTRIPs targeted to the genomic RNA of hRSV were used in conjunction with a GFP-TIA-1 fusion protein in infected A549 cells, to evaluate the interaction between the stress granule protein TIA-1 and hRSV viral RNA when stress granules were induced by sodium arsenite treatment. Previous findings demonstrated that paramyxovirus RNA, which contains many possible TIA-1 or TIAR binding sites (uracil-rich regions), likely interacts with stress granules; this interaction though, has not been characterized in living cells. In hRSV-infected cells transfected with GFP-TIA-1, stress granules had not formed 24 h after infection as identified by the lack of aggregation of GFP-TIA-1 in cells also containing viral RNA (FIG. 3a). MTRIPs were specific and did not aggregate RNA (FIGS. 8-10).

More specifically, in order to show that these probes can target viral RNA molecules specifically within living cells, MTRIPs targeted to the genomic RNA of hRSV and β-actin mRNA were assembled, delivered via SLO into infected and non-infected cells, fixed in paraformaldehyde post-hybridization and stained for known RNA binding proteins or colocalized molecules. This experiment was performed in order to confirm the probes were binding to functional, biologically relevant populations of RNA. Intensity profiles, as well as merged images from a single image plane, are displayed to show RNA-protein colocalization. A single probe was used to target the gene-end-intergenic-gene-start sequence of the hRSV genome, which has 3 exact repeats 7 (see Table 1). When delivered at 30 nM concentrations, localized signal was observed within 10 minutes. Following fixation and staining, the RNA signal was observed to be colocalized (yellow) with the nucleocapsid (N) protein, in the infected A549 cells. This colocalization was observed in the merged image as well as in an intensity profile intersecting granules (FIG. 8a-b), while in the non-infected cells, only background signal was evident (FIG. 8c-d). The hRSV N protein was chosen because it is known to associate strongly with hRSV viral genomic RNA. This experiment was repeated and followed by 3D imaging with a laser scanning confocal microscope; 2D images were reconstructed in 3D in Improvision's Volocity software (FIG. 9). From the overlap of voxels generated in Volocity, the Manders overlap coefficient was calculated as 0.65, clearly indicating colocalization in three dimensions between the viral RNA detected with MTRIPs and the nucleocapsid protein.

Tetravalent MTRIPs and monovalent probes (single multiply-labeled ligand) both targeted to hRSV genomic RNA were delivered via SLO, each at 30 nM, into separate wells of A549 cells, each infected from the exact same vial of virus, 24 hrs post-infection. The cells were then fixed in 4% paraformaldehyde and imaged via laser scanning confocal. From the reconstructed 3D images of the cells (see extended view images of the cells in FIG. 10a), the number of viral RNA granules could be counted for each probe type. It should be noted that even though the number of granules detected is statistically similar via the Wilcoxon-Mann-Whitney test, the photomultiplier voltage on the laser scanning confocal microscope was approximately 4 times higher for the monovalent probe, which was expected. By combining 4 ligands, the resulting MTRIPs were 4 times brighter, a necessity for the live-cell imaging in FIG. 3. From the results of counting RNA granules from over 30 cells (FIG. 10b) for both the tetravalent and monovalent probes, the statistical similarity of the two populations could be estimated using the Wilcoxon-Mann-Whitney test. From this test, the resulting p value of 0.87 was determined, which conclusively demonstrates that the samples originated from the same population. This conclusively shows that MTRIPs do not significantly aggregate RNA; RNA aggregation would have resulted in the detection of different numbers of RNA granules.

To induce stress granules, the cells were exposed to 1.0 mM sodium arsenite and substantial transient interactions were observed between stress and viral RNA granules (FIG. 3b-d). A stress granule was observed moving into a viral RNA granule and residing within it for over a minute before it was released (FIG. 3c). Another stress granule then appeared to dock with a viral RNA granule (FIG. 3d), and appeared to be in contact for approximately 45 s. Transient interactions between RNA granules on the same time scales had been reported, supporting our observations, but previously engineered RNAs or proteins were imaged, in contrast to the non-engineered RNAs imaged in this study. More stable interactions were observed between GFP-TIA-1 and the viral RNA (FIGS. 11 and 12).

In addition to the transient behavior shown in FIG. 3, GFP-TIA-1 was also notably visible on some of the viral RNA granules approximately 20 to 30 minutes after sodium arsenite treatment. Their association was confirmed by capturing video images of RNA granules during both a fusion (FIG. 11) and splitting event (FIG. 12), and observing the protein follow the same dynamic course as the RNA. The overlap is not perfect, suggesting that only some of the RNA in the granule may be in contact with GFP-TIA-1, but the association is quite obvious. This finding suggests that there may be multiple mechanisms by which TIA-1 interacts with RNA, in a transient, granule-granule manner (FIG. 3), which may depend on granule size, and also through a more stable event, driven by RNA-protein binding.

In this Example, we demonstrated that MTRIPs have single-molecule sensitivity and can be used to target and follow native and nonengineered RNA granules in living cells, in both a cell line and a primary fibroblast using streptolysin O delivery; streptolysin O delivery induced only minimal cell death (FIG. 13) and did not change cellular morphology appreciably or induce stress granules. Owing to their brightness at multiple wavelengths, small size and ease of assembly, these probes should be broadly applicable for studying single-molecule RNA-related events in living cells. To this end, a standard live/dead viability/cytotoxicity assay (Invitrogen L-3224) was performed to assess the effect of SLO on A549 cells (FIG. 13). The assay was performed on normally growing cells and cells exposed to 0.2 U/ml of activated SLO for 10 minutes. From the results in FIG. 13, it can be seen that SLO exposure does not change cell morphology and is associated with minimal cell death (green cells are living while red cells are dead). From statistics generated from over 700 cells in each group, 98.85 percent of the cells that were not exposed to SLO were alive, while 96.85 percent were alive after SLO exposure. SLO was associated with only a two percent increase in cell death over the normally growing cells. This is consistent with a previous live/dead assay performed on Hela cells reported by Paillasson et al. (1997). They reported 95% alive in normally growing cells, and 93% alive when exposed to SLO8.

Example 2

Single Molecule Sensitive Multivalent Polyethylene Glycol Probes for RNA Imaging The below Example was published in *Bioconjugate Chemistry*, Vol. 21. No. 3 (February 2010). Consequently the referenced Figures can be viewed in color in this publication, which is hereby incorporated by reference.

Single molecule imaging of native and nonengineered RNAs in live cells has recently been achieved by the use of multiply labeled tetravalent RNA imaging probes (MTRIPs). These probes consist of four fluorescently labeled linear oligonucleotides bound together by a biotin-streptavidin linkage and recognize their intracellular target RNA through Watson-Crick base pairing. Signal is raised above background by the binding of 2-3 probes per target RNA and through the natural localization of the target RNA. Prior to the introduction of MTRIPs, single molecule studies of specific RNA localization and transport in live cells were limited to plasmid derived RNAs either containing binding site repeats for the MS2-GFP fusion protein or containing binding site repeats for a molecular beacon. Plasmid derived RNAs offer tremendous methodological flexibility, but they preclude the study of native RNA or nonengineered viral RNA and do not allow for imaging native RNAs in vivo.

While MTRIPs have proven to be capable of targeting a number of RNAs in various cell types with single RNA sensitivity, the use of a streptavidin core imparts some limitations. Probes with a streptavidin core have a maximum of four noncovalently bound ligands, which limits the number of fluorophores that can be added to a single probe. Streptavidin also contributes significantly to the molecular weight of the probe (~53 kDa) and might affect the delivery pathway during cell penetrating peptide-mediated delivery. In this Example, we report the synthesis and application of a multivalent RNA imaging probe that utilizes an eight-armed poly(ethylene glycol) (PEG) core. These probes overcome the main limitations imposed by streptavidin by increasing the number of bound ligands while reducing the molecular weight of the core (20 kDa). Moreover, the probes are stabilized by employing a covalent bond between the ligand and the core. PEG was chosen, since it has been shown to reduce toxicity, reduce nonspecific binding, and improve internalization when conjugated to macromolecules and utilized in vivo.

In order to demonstrate the efficiency of probe delivery and targeting, we utilized the genomic viral RNA (vRNA) of human respiratory syncytial virus (hRSV) as a model system. The localization of the vRNA of hRSV has been previously characterized by both molecular beacons and MTRIPs and showed high concentrations of viral RNA in cytoplasmic foci termed inclusion bodies. Delivery of probe into live cells was achieved using reversible membrane permeabilization with streptolysin O (SLO), which has been shown to allow for efficient and homogeneous delivery of macromolecules into the cytoplasm. The use of SLO results in ~100% probe delivery efficiency and results in minimal cytotoxicity. Alternatively, as a delivery strategy, we also used the cell penetrating peptide (CCP) TAT, which, when conjugated to macromolecules, has been shown to transduce them across the plasma membrane. Indeed, the use of the PEG core permits an increase in the number of bound ligands and allows for the conjugation of delivery and targeting peptides along with RNA targeting oligonucleotides, while maintaining single molecule sensitivity. CPP-conjugated probes are currently of great interest in molecular imaging since they have the advantage of being suitable for use in vivo when labeled with near-infrared fluorophores. As with SLO, CPP based delivery allows for ~100% delivery efficiency and low cytotoxicity at low concentrations and eliminates the need for permeabilization of the membrane, reducing the complexity of the experimental procedure.

Materials and Methods.

Multivalent PEG Probes.

2'-O-Me RNA/DNA chimeric oligonucleotides were synthesized by Biosearch Technologies, Inc. (Novato, Calif.) with the following sequence, (SEQ ID NO 12) 5'-UXTXT-TXAAAAAXGGGGCAAAXAA-3', where the boldface type is 2'-O-Methyl RNA, the X is a dT-C6-NH2, the 5'-U contains a free thiol group, and all others are DNA. The binding region is underlined.

Structure of the internal amine modified thymidines

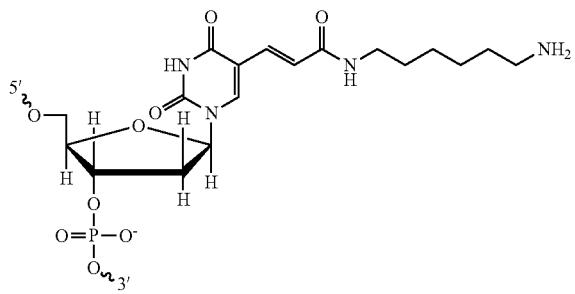

Structure of the 5' thiol modified 2'-O-Methyl Uridine

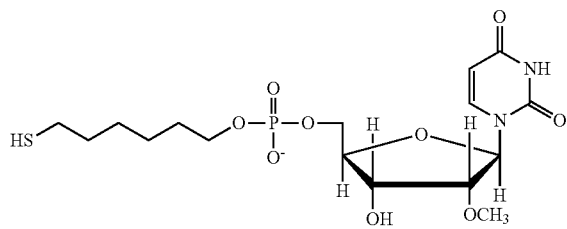

Probes were synthesized by first labeling the individual ligands with amine reactive NHS ester fluorophores Atto 488 (ATTO-TEC GmbH), Cy3B (GE Healthcare), or Atto 647N (ATTO-TEC GmbH) using the manufacturer's protocols. Ligands were subsequently linked to 20 kDa eight-armed maleimide poly(ethylene glycol) (8-Arm PEG) cores (NOF America) by incubation in a 64:1 molar ratio in PBS (Ambion) and 1 mM EDTA (Ambion) for 12 h at room temperature. 8-Armed PEG probes with TAT were synthesized by adding ligand, Cys-TAT (Anaspec, Cys-TAT 47-57), and 8-Arm-PEG cores in a 64:8:1 molar ratio in 10×PBS, and 1 mM EDTA for 12 h at room temperature. All probes were filtered to remove free ligand and reaction buffer using 30 kDa molecular weight cutoff Nanosep centrifugal devices (Pall Corp.). Purified probes were resuspended in nuclease free PBS and stored at 4° C.

Structure of the 8-Arm maleimide activated PEG

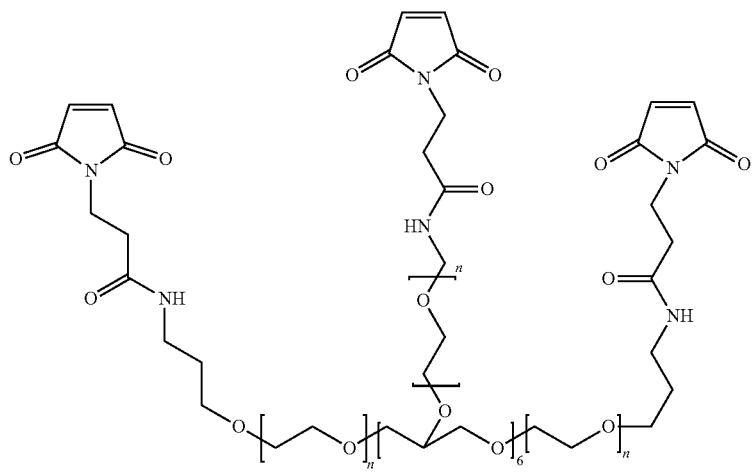

Cells and Virus.

A549 human lung carcinoma cells (ATCC CCL-185) were cultured in DMEM (Lonza) with 10% FBS (Hyclone), 100 U/mL penicillin, and 100 U/mL streptomycin (Invitrogen). Cells were plated on glass coverslips one day prior to experiments. The A2 strain of human respiratory syncytial virus (hRSV) (Crowe laboratory, Vanderbilt University) was used at a MOI) 1 and a titer of 1×106 TCID50 mL-1.

Probe Delivery.

Probes were delivered into A549 cells using reversible membrane permeabilization and peptide mediated delivery. For reversible membrane permeabilization, 2 U/mL Streptolysin O (SLO) (Sigma) were first reduced using 7.5 mM Tris (2-carboxyethyl)phosphine (TCEP) (Peirce) for 1 h at 37° C. Infected and noninfected cells were rinsed using PBS ($-Ca^{2+}-Mg^{2+}$) (Thermo) and then incubated with delivery medium containing 0.2 U/mL SLO and 5 nM probe in PBS ($-Ca^{2+}-Mg^{2\pm}$) for 10 mM at 37° C. The delivery medium was then removed and replaced with complete growth media for 15 min. For TAT mediated delivery of probes, infected and noninfected cells were incubated in complete medium containing 5 nM TAT conjugated probe for 10 mM at 37° C., after which it was replaced with complete medium for 15 mM For live cell imaging experiments, growth media was replaced with Leibovitz's L15 medium (Invitrogen) immediately prior to image acquisition.

Immunostaining.

After probe delivery, cells were rinsed in PBS (Ambion), fixed with 4% paraformaldehyde (Electron Microscopy Science) in PBS, permeabilized using 0.2% Triton-X 100 (Sigma), and blocked with 5% bovine serum albumin (Ambion). Cells were then incubated with a mouse monoclonal primary antibody against the hRSV N Viral Protein (Abcam), CD63 (Developmental Studies Hybridoma Bank), or LAMP-1 (Developmental Studies Hybridoma Bank) for 30 mM at 37° C. and with a goat anti-mouse secondary antibody labeled with Alexa 488 (Invitrogen) for 30 min at 37° C. After DAPI staining (Invitrogen), cells were mounted on slides using PVA with DABCO (Sigma).

Fluorescence Imaging.

Samples were imaged using a Zeiss Axiovert 200 M epifluorescent microscope with a 63×=1.4 NA Plan-Apochromat objective, using Chroma 49002 ET-GFP (FITC/Cy2), 49004 ET Cy3, 49006 ET Cy5 filter sets, an EXFO excite 120 for fluorescence excitation, a Polytek PI objective piezo for taking stacks of images, and a Hamamatsu ORCAER AG for capturing digital images. Image z-stacks were acquired in 200 nm steps using Volocity (Improvision). Exposure times for probes on glass (FIG. 15) were approximately 500 ms. Exposure times for probes in endosomal and lysosomal marker colocalization studies were 400 ms for noninfected cells (FIG. 16c-d) and 30 ms for infected cells (FIG. 16e-f). Exposure times for RSV vRNA in infected cells and controls, both fixed and live, were approximately 100 ms (FIGS. 17-18). Identical exposure times in FIGS. 17 and 18 were used for comparison of intensities.

Image Analysis.

All images were deconvolved using the iterative restoration algorithm in Volocity. Histograms of mean fluorescence intensity were generated by identifying objects with minimum and maximum intensities set to 4 SD and 100 SD, respectively. Objects smaller than 1 point spread function were removed. Intensity Profiles were generated using Image) (NIH) Color Profiler plug-in and data tables were imported into Sigma Plot 11 (Systat Software Inc.) for plotting. Manders overlap coefficient was calculated using Volocity software.

Determination of the Degree of Labeling.

The degree of labeling (DOL) of the oligonucleotides, i.e. the average number of dyes per oligonucleotide, was determined by measuring the UV-VIS spectrum of the conjugate solution in a quartz cuvette in order to obtain the absorbance at the absorption maximum of the dye and at 260 nm. The concentrations of the oligonucleotides and the dyes were calculated using the Lambert-Beer law and the extinction coefficients provided by the manufacturers (FIG. 19a). The average number of labeled oligonucleotides per activated PEG was estimated by measuring the conjugate absorbance at the absorption maximum of the dye and dividing it by the previously determined DOL (FIG. 19b). The same procedure was used to determine the average number of labeled oligonucleotides conjugated to the PEG-TAT probes (FIG. 19c). The average number of TAT peptides per PEG molecule was determined by absorption spectroscopy after conjugation to PEG of unlabeled oligonucleotides and fluorescein-labeled Cys-TAT (Cys-TAT-FAM, Anaspec) (FIG. 19d).

In order to validate our estimation of probe concentrations and ensure that unconjugated oligonucleotides were adequately removed upon filtration, gel electrophoresis was performed (FIG. 20) using 15% TBE-UREA gels according to manufacturer's protocols (Invitrogen). Analysis showed that less than 10% of the unbound oligonucleotides contribute to the absorption spectroscopy measurements after filtration. Unfortunately, gel electrophoresis did not prove to be useful to investigate the homogeneity of the conjugates, due to the lack of clear bands. However, analysis of the microscopy data in FIG. 2 showed that the mean fluorescence intensity of single probes had a measured standard deviation of about 5% of the mean.

Results and Discussion hRSV specific ligands were composed of 2'-O-Methyl-RNA and DNA chimeric oligonucleotides with five amine-modified thymidines and a 5' thiol modification. The oligonucleotide sequence was designed to be complementary to a gene-end-intergenic-gene-start sequence of hRSV which has three exact repeats in the hRSV genome and is not present in the human genome. The sequence used has previously been shown to be accessible by antisense knockdown experiments, molecular beacon imaging, and MTRIP imaging. The targeting of three repeats per RNA raises signal significantly above background for even a single RNA per point spread function.

The amine-modified thymidines of the ligands were used to conjugate NHS-ester fluorophores, and the thiol group was used to link the individual ligands to the PEG cores, which were functionalized with eight maleimide active groups (FIG. 14a). Absorption spectroscopy showed that, on average, 3 dyes were conjugated to each ligand and 6.5 ligands were conjugated to each PEG core. Probes utilizing the TAT CPP contained an average of 4 oligonucleotides ligands and 1 TAT peptide. By increasing the brightness of the probes through the use of multiple ligands, rather than increasing the number of fluorophores per ligand, self-quenching was minimized and ligand size was kept to approximately 20 bases. The fluorophores (Atto 488, Cy3B, and Atto 647N) were chosen for their strong absorption in visible wavelengths commonly used for imaging, high quantum efficiency, and low triplet state excitation. The use of ligands with a 2'-O-Methyl backbone conferred increased affinity for the target mRNA, increased signal-to-noise ratio, and nuclease resistance.

In order to test the ligands for nonspecific aggregation, the probes were labeled with Atto 488, Cy3B, or Atto 647N fluorophores and were adsorbed onto a cover glass at 1 nM concentration. Using wide-field fluorescence microscopy, the probes were visible as distinct spots on the glass without apparent aggregation (FIG. 15a). Lack of aggregation was confirmed both by fluorescence intensity histograms (FIG. 15b-d) and by the lack of colocalization of probes labeled with different fluorophores. When the probes were delivered at 5 nM to include all the relevant signal within the three-dimensional cell. The uniformity of the signal within the cytoplasm indicated that probe was not aggregating due to nonspecific interaction with cellular components.

Recent reports have shown that macromolecule uptake by TAT can proceed through an endocytic pathway, even if this has been suggested to be dependent upon the conjugated macromolecule. Nonendosomal transduction of the probes is recommended, since it reduces the exposure of the probe to nucleases and eliminates the need for endosomal releasing agents such as poly(propylacrylic acid) to be added to the delivery medium. In order to determine whether or not TAT conjugated probes entered cells through the endosomal pathway, TAT-probes were delivered at 5 nM into uninfected and hRSV infected cells that were subsequently fixed and immunostained for endosomal and lysosomal markers. Cells were immunostained for cluster of differentiation 63 (CD63) (FIG. 16c,e) and lysosomal associated membrane protein 1 (LAMP1) (FIG. 16d,f). Multicolor images were obtained by wide-field fluorescence microscopy and deconvolution, and revealed little colocalized signal between the TAT-conjugated probe and protein markers. In these figures, extended views were shown to illustrate the signal within the cell. Some apparent colocalization may be perceived using this presentation due to the merging of signal from different z-planes. Inset images from one z-plane were included to show the lack of colocalization qualitatively. This was confirmed quantitatively by low Manders overlap coefficients (R<0.1) for the colocalization of the probe with CD63 and with LAMP1 using three-dimensional reconstructions of the images.

In order to demonstrate the applicability of these probes for live cell imaging, the viral genomic RNA of hRSV was imaged in A549 cells both live and after fixation and immunostaining of the hRSV N protein. The hRSV N protein has been shown to reside within inclusion bodies, to colocalize with the hRSV genome in imaging experiments, and to bind to hRSV vRNA. Co-localization with the N protein served to demonstrate the accurate targeting of the probe to the vRNA. A549 cells were infected with the A2 strain of hRSV and incubated for 24 h. Probes were then delivered at 5 nM via SLO membrane permeabilization and allowed to recover. Subsequently, cells were either fixed with 4% paraformaldehyde for immunostaining or stained with Hoechst 33342 for live cell imaging. Cells fixed and immunostained for the hRSV N protein showed vRNA localization near the plasma membrane and exhibited colocalization with hRSV N protein similar to previously reported data (FIG. 17a). In order to quantify the degree of colocalization between the vRNA and N protein, Manders overlap coefficients were generated using voxel intensities. Overlap coefficients were generally high, typically R>0.8. FIG. 17a shows a representative cell with an overlap coefficient of 0.843. In addition to whole cell automatic colocalization, intensity profiles showed correlation between the hRSV genomic and N protein signal (FIG. 17c, d). In the live cell images, similar localization of the vRNA was observed with vRNA predominantly residing in inclusion bodies close to the cell membrane (FIG. 17e). Delivery of probe into noninfected cells served as a negative control and resulted in little to no signal when imaged under the same conditions as the infected cells (FIG. 17b,f). Interestingly, probes delivered into noninfected cells demonstrated no significant nuclear background.

We subsequently delivered the TAT conjugated probes at 5 nM concentration into hRSV infected and noninfected A549 cells. These probes revealed a similar pattern of RNA localization as the SLO-delivered ones in infected cells both live and upon fixation. In the latter case, colocalization with the viral N protein at the plasma membrane confirmed efficient vRNA targeting (FIG. 18a,c,d). In noninfected cells, TAT-conjugated probes exhibited little to no signal (FIG. 18b) and appeared to be homogeneously distributed in the cytoplasm (FIG. 16b). While the mechanism for TAT-mediated probe delivery is not yet fully understood, our data strongly suggest that it does not involve an endosomal pathway and are consistent with previous reports. In particular, Vives et al. reported that fluorescently labeled TAT peptides were efficiently taken up by cells within 5 min at concentrations as low as 100 nM, and the internalization process was shown not to involve an endocytic pathway. The sensitivity of the fluorescein reporter precluded measurements using TAT concentrations below 100 nM. In our case, uptake of probes occurred in less than 10 min at a concentration of 5 nM. Moreover, our probes showed no colocalization with endosomal and lysosomal markers, and colocalized well with the N protein, yielding a distribution similar to the one observed in SLO membrane permeabilization-based delivery. Additionally, live cell imaging experiments confirmed the results and indicated that cell fixation does not later probe localization.

CONCLUSION

The importance of trans-acting factors, such as RNA binding proteins and noncoding RNAs, in the regulation of mRNA and viral RNAs has recently garnered increased attention. These factors are responsible for the post-translational regulation of mRNAs and for the late stages of the viral life cycle such as replication and packaging of viral genomic RNA. The RNA molecule, along with trans-acting factors, ultimately determines the function of the RNA. In vitro methods for studying these ribonucleoprotein complexes (RNPs) give only an averaged view of the function of these complexes. However, within the cellular context, these RNPs are often heterogeneous, and as such, methods are needed that enable the study of the spatial and temporal dynamics of RNA and interaction with RNA binding proteins within the cell. These methods must be sensitive because of the low concentration of specific RNAs inside the cell, and must be able to provide accurate subcellular localization of RNA.

Using an eight-arm activated PEG core as a multifunctional platform, we have developed a single molecule sensitive RNA imaging probe. Fluorescently labeled oligonucleotides bound to the PEG core were delivered into live cells using two delivery methods, reversible membrane permeabilization and TAT-mediated transduction. Individual probes were visible both on glass and inside the cells using widefield fluorescence microscopy. TAT-mediated delivery did not result in accumulation of probes in endosomes, nor did it result in the nonspecific aggregation of probes inside the cell. To demonstrate the accurate targeting of RNA in the cell, probes targeted against RSV vRNA were delivered into infected cells and demonstrated subcellular localization at the plasma membrane, colocalization with known vRNA binding proteins, and signal substantially higher than in mock infected controls. Signal was observed in less than 10 min regardless of the delivery method and in the presence of probe concentrations of 5 nM. The rapid binding of the probes to their target is an essential feature for the study of RNA dynamics, because it allows for the observation of phenomena that occur on short time scales. In addition to this, the low concentration of the probes contributes to reduce nonspecific binding. Our results suggest that TAT (or other CPPs) conjugated PEG probes may allow for the imaging of specific RNAs in vivo when combined with fluorophores that absorb in the near-infrared wavelengths.

What is claimed is:

1. A biomolecule probe comprising:
    a multivalent core comprising a plurality of attachment sites;
    a plurality of RNA/DNA chimeric linear oligonucleotides having specificity for a target, wherein the plurality of RNA/DNA chimeric linear oligonucleotides are each bound to an attachment site of the multivalent core; and
    a plurality of reporter molecules, wherein each reporter molecule is bound to the RNA/DNA chimeric linear oligonucleotide.

2. The biomolecule probe of claim 1, wherein a ratio of the plurality of RNA/DNA chimeric linear oligonucleotides to the plurality of attachment sites on the multivalent core is equal to or less than about 1.

3. The biomolecule probe of claim 1, wherein a ratio of reporter molecule to plurality of RNA/DNA chimeric linear oligonucleotides is greater than or equal to about 1.

4. The biomolecule probe of claim 3, wherein the ratio of reporter molecule to the plurality of RNA/DNA chimeric linear oligonucleotides is about 3.

5. The biomolecule probe of claim 4, wherein the target is a RNA.

6. The biomolecule probe of claim 4, wherein the reporter molecule comprises a fluorophore.

7. The biomolecule probe of claim 3, wherein the nucleic acid comprises an attachment region, a spacer region, and a hybridization region.

8. The biomolecule probe of claim 3, wherein multivalent core comprises avidin or a derivative thereof.

9. The biomolecule probe of claim 3, wherein multivalent core comprises a multivalent polyethylene glycol core.

10. The biomolecule probe of claim 9, further comprising a peptide, wherein the peptide is bound to an attachment site of the multivalent polyethylene glycol core.

11. The biomolecule probe of claim 10, wherein the peptide comprises a targeting moiety.

12. The biomolecule probe of claim 10, wherein the peptide comprises an epitope moiety.

13. A RNA imaging probe comprising:
    a multivalent core comprising a plurality of attachment sites;
    a plurality of RNA/DNA chimeric linear oligonucleotides having a specificity for a plurality of sites on a target RNA, wherein a RNA/DNA chimeric linear oligonucleotide is bound to an attachment site of the multivalent core; and
    a plurality of fluorophores, wherein a fluorophore is bound to the RNA/DNA chimeric linear oligonucleotide.

14. The RNA imaging probe of claim 13, wherein a ratio of fluorophore to RNA/DNA chimeric linear oligonucleotide is greater than 1.

15. The RNA imaging probe of claim 14, wherein a ratio of fluorophore to RNA/DNA chimeric linear oligonucleotide is greater than or equal to about 3.

16. The RNA imaging probe of claim 13, wherein the RNA/DNA chimeric linear oligonucleotide comprises an attachment region, a spacer region, and a hybridization region.

17. The RNA imaging probe of claim 16, wherein multivalent core comprises a tetravalent strepavidin core, and wherein the attachment region of the RNA/DNA chimeric linear oligonucleotide comprises biotin.

18. The RNA imaging probe of claim 16, wherein multivalent core comprises a multivalent polyethylene glycol core, and wherein the attachment group comprises a 5' thiol modified 2'-O-methyl uridine.

19. The RNA imaging probe of claim 16, wherein the spacer region comprises a plurality of deoxythymidines, a plurality of deoxyadenonsines, or combinations thereof.

20. The RNA imaging probe of claim 16, wherein the RNA/DNA chimeric linear oligonucleotide further comprises a plurality of amino-modified deoxythymidines.

21. The RNA imaging probe of claim 13 further comprising a targeting moiety.

22. The RNA imaging probe of claim 13 further comprising an epitope moiety.

23. A method for detecting a single molecule of RNA using the RNA imaging probe of claim 13 comprising:
    delivering an effective amount of the RNA imaging probe to a cell; and
    detecting a molecule of a target RNA in a cell.

24. The method for detecting a single molecule of RNA of claim 23, wherein the effective amount of an RNA imaging probe has a concentration of less than about 1 micromolar ($\mu$M).

25. The method for detecting a single molecule of RNA of claim 24, wherein the effective amount of an effective amount of an RNA imaging probe has a concentration ranging from about 5 nanomolar (nM) to about 30 nanomolar (nM).

26. The method for detecting a single molecule of RNA of claim 23, wherein the delivering an effective amount of an RNA imaging probe to a cell comprises permeabilizing the cell with streptolysin 0.

27. The method for detecting a single molecule of RNA of claim 23, wherein the delivering an effective amount of an RNA imaging probe to a cell comprises microinjecting the RNA imaging probe into a cell.

28. The method for detecting a single molecule of RNA of claim 23, wherein the detecting a molecule of a RNA in a cell comprises visualizing the association of the RNA imaging probe with the molecule of a target RNA in a cell through microscopy.

29. The method for detecting a single molecule of RNA of claim 23, wherein the RNA is a native, non-engineered RNA.

30. The method for detecting a single molecule of RNA of claim 23, wherein the RNA is a cellular RNA.

31. The method for detecting a single molecule of RNA of claim 30, further comprising detecting a protein that is associated with the target RNA.

32. The method for detecting a single molecule of RNA of claim 23, wherein the RNA is a viral RNA.

* * * * *

SEQUENCE LISTING

<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Cys Gly Pro Glu Asn Gly Arg Arg Gly Gly Phe Gly Ser Arg Gly
1               5                   10                  15

<210> SEQ ID NO 2
<211> LENGTH: 24
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base

```
<222> LOCATION: (1)..(1)
<223> OTHER INFORMATION: 2'-O-Methyl
<220> FEATURE:
<221> NAME/KEY: modified_base
<222> LOCATION: (2)..(2)
<223> OTHER INFORMATION: dT-C6-NH2
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: modified_base
<222> LOCATION: (4)..(4)
<223> OTHER INFORMATION: dT-C6-NH2
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: modified_base
<222> LOCATION: (7)..(7)
<223> OTHER INFORMATION: dT-C6-NH2
<220> FEATURE:
<221> NAME/KEY: misc_feature
<222> LOCATION: (7)..(7)
<223> OTHER INFORMATION: n is a, c, g, t or u
<220> FEATURE:
<221> NAME/KEY: modified_base
<222> LOCATION: (8)..(12)
<223> OTHER INFORMATION: 2'-O-Methyl
<220> FEATURE:
<221> NAME/KEY: modified_base
<222> LOCATION: (13)..(13)
<223> OTHER INFORMATION: dT-C6-NH2
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: modified_base
<222> LOCATION: (14)..(21)
<223> OTHER INFORMATION: 2'-O-Methyl
<220> FEATURE:
<221> NAME/KEY: modified_base
<222> LOCATION: (22)..(22)
<223> OTHER INFORMATION: dT-C6-NH2
<220> FEATURE:
<221> NAME/KEY: misc_feature
<222> LOCATION: (22)..(22)
<223> OTHER INFORMATION: n is a, c, g, t or u
<220> FEATURE:
<221> NAME/KEY: modified_base
<222> LOCATION: (23)..(24)
<223> OTHER INFORMATION: 2'-O-Methyl

<400> SEQUENCE: 2
untnttnaaa aanggggcaa anaa                                          24

<210> SEQ ID NO 3
<211> LENGTH: 23
<212> TYPE: DNA
<213> ORGANISM: Artificial Sequence
<220> FEATURE:
<223> OTHER INFORMATION: nucleic acid probe
<220> FEATURE:
<221> NAME/KEY: modified_base
<222> LOCATION: (1)..(1)
<223> OTHER INFORMATION: 2'-O-Methyl
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (2)..(2)
<223> OTHER INFORMATION: dT-C6-NH2
<220> FEATURE:
```

<221> NAME/KEY: misc_feature
<222> LOCATION: (2)..(2)
<223> OTHER INFORMATION: n is a, c, g, t or u
<220> FEATURE:
<221> NAME/KEY: modified_base
<222> LOCATION: (6)..(6)
<223> OTHER INFORMATION: dT-C6-NH2
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: modified_base
<222> LOCATION: (7)..(7)
<223> OTHER INFORMATION: 2'-O-Methyl
<220> FEATURE:
<221> NAME/KEY: modified_base
<222> LOCATION: (8)..(8)
<223> OTHER INFORMATION: dT-C6-NH2
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: modified_base
<222> LOCATION: (9)..(17)
<223> OTHER INFORMATION: 2'-O-Methyl
<220> FEATURE:
<221> NAME/KEY: modified_base
<222> LOCATION: (18)..(18)
<223> OTHER INFORMATION: dT-C6-NH2
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: modified_base
<222> LOCATION: (19)..(21)
<223> OTHER INFORMATION: 2'-O-Methyl
<220> FEATURE:
<221> NAME/KEY: modified_base
<222> LOCATION: (22)..(22)
<223> OTHER INFORMATION: dT-C6-NH2
<220> FEATURE:
<221> NAME/KEY: misc_feature
<222> LOCATION: (22)..(22)
<223> OTHER INFORMATION: n is a, c, g, t or u
<220> FEATURE:
<221> NAME/KEY: modified_base
<222> LOCATION: (23)..(23)
<223> OTHER INFORMATION: 2'-O-Methyl

<400> SEQUENCE: 3
untttnanag cacagccngg ana                                             23

<210> SEQ ID NO 4
<211> LENGTH: 25
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (7)..(7)
<223> OTHER INFORMATION: dT-C6-NH2
<220> FEATURE:
<221> NAME/KEY: misc_feature
<222> LOCATION: (7)..(7)
<223> OTHER INFORMATION: n is a, c, g, t or u
<220> FEATURE:
<221> NAME/KEY: modified_base
<222> LOCATION: (8)..(10)
<223> OTHER INFORMATION: 2'-O-Methyl

```
<220> FEATURE:
<221> NAME/KEY: modified_base
<222> LOCATION: (11)..(11)
<223> OTHER INFORMATION: dT-C6-NH2
<220> FEATURE:
<221> NAME/KEY: misc_feature
<222> LOCATION: (11)..(11)
<223> OTHER INFORMATION: n is a, c, g, t or u
<220> FEATURE:
<221> NAME/KEY: modified_base
<222> LOCATION: (12)..(16)
<223> OTHER INFORMATION: 2'-O-Methyl
<220> FEATURE:
<221> NAME/KEY: modified_base
<222> LOCATION: (17)..(17)
<223> OTHER INFORMATION: dT-C6-NH2
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: modified_base
<222> LOCATION: (18)..(23)
<223> OTHER INFORMATION: 2'-O-Methyl
<220> FEATURE:
<221> NAME/KEY: modified_base
<222> LOCATION: (24)..(24)
<223> OTHER INFORMATION: dT-C6-NH2
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: modified_base
<222> LOCATION: (25)..(25)
<223> OTHER INFORMATION: 2'-O-Methyl

<400> SEQUENCE: 4 tttttnauu ncccgcncgg ccgng                                        25

<210> SEQ ID NO 5
<211> LENGTH: 26
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (6)..(6)
<223> OTHER INFORMATION: dT-C6-NH2
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: modified_base
<222> LOCATION: (7)..(10)
<223> OTHER INFORMATION: 2'-O-Methyl
<220> FEATURE:
<221> NAME/KEY: modified_base
<222> LOCATION: (11)..(11)
<223> OTHER INFORMATION: dT-C6-NH2
<220> FEATURE:
<221> NAME/KEY: misc_feature
<222> LOCATION: (11)..(11)
<223> OTHER INFORMATION: n is a, c, g, t or u
<220> FEATURE:
<221> NAME/KEY: modified_base
<222> LOCATION: (12)..(18)
<223> OTHER INFORMATION: 2'-O-Methyl
<220> FEATURE:
<221> NAME/KEY: modified_base
<222> LOCATION: (19)..(19)
```

-continued

<223> OTHER INFORMATION: dT-C6-NH2
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: modified_base
<222> LOCATION: (20)..(22)
<223> OTHER INFORMATION: 2'-O-Methyl
<220> FEATURE:
<221> NAME/KEY: modified_base
<222> LOCATION: (23)..(23)
<223> OTHER INFORMATION: dT-C6-NH2
<220> FEATURE:
<221> NAME/KEY: misc_feature
<222> LOCATION: (23)..(23)
<223> OTHER INFORMATION: n is a, c, g, t or u
<220> FEATURE:
<221> NAME/KEY: modified_base
<222> LOCATION: (24)..(26)
<223> OTHER INFORMATION: 2'-O-Methyl

<400> SEQUENCE: 5
tttttnggag naacgcggnc agncag                                        26

<210> SEQ ID NO 6
<211> LENGTH: 25
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (3)..(3)
<223> OTHER INFORMATION: dT-C6-NH2
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: modified_base
<222> LOCATION: (7)..(9)
<223> OTHER INFORMATION: 2'-O-Methyl
<220> FEATURE:
<221> NAME/KEY: modified_base
<222> LOCATION: (10)..(10)
<223> OTHER INFORMATION: dT-C6-NH2
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: modified_base
<222> LOCATION: (11)..(14)
<223> OTHER INFORMATION: 2'-O-Methyl
<220> FEATURE:
<221> NAME/KEY: modified_base
<222> LOCATION: (15)..(15)
<223> OTHER INFORMATION: dT-C6-NH2
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: modified_base
<222> LOCATION: (16)..(21)
<223> OTHER INFORMATION: 2'-O-Methyl
<220> FEATURE:
<221> NAME/KEY: modified_base
<222> LOCATION: (22)..(22)
<223> OTHER INFORMATION: dT-C6-NH2
<220> FEATURE:
<221> NAME/KEY: misc_feature
<222> LOCATION: (22)..(22)
<223> OTHER INFORMATION: n is a, c, g, t or u
<220> FEATURE:
<221> NAME/KEY: modified_base
<222> LOCATION: (23)..(25)
<223> OTHER INFORMATION: 2'-O-Methyl

<400> SEQUENCE: 6
ttntttcaan aucancaucc anggc                                    25

<210> SEQ ID NO 7
<211> LENGTH: 27
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (6)..(6)
<223> OTHER INFORMATION: dT-C6-NH2
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: modified_base
<222> LOCATION: (7)..(10)
<223> OTHER INFORMATION: 2'-O-Methyl
<220> FEATURE:
<221> NAME/KEY: modified_base
<222> LOCATION: (11)..(11)
<223> OTHER INFORMATION: dT-C6-NH2
<220> FEATURE:
<221> NAME/KEY: misc_feature
<222> LOCATION: (11)..(11)
<223> OTHER INFORMATION: n is a, c, g, t or u
<220> FEATURE:
<221> NAME/KEY: modified_base
<222> LOCATION: (12)..(14)
<223> OTHER INFORMATION: 2'-O-Methyl
<220> FEATURE:
<221> NAME/KEY: modified_base
<222> LOCATION: (15)..(15)
<223> OTHER INFORMATION: dT-C6-NH2
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: modified_base
<222> LOCATION: (16)..(18)
<223> OTHER INFORMATION: 2'-O-Methyl
<220> FEATURE:
<221> NAME/KEY: modified_base
<222> LOCATION: (19)..(19)
<223> OTHER INFORMATION: dT-C6-NH2
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: modified_base
<222> LOCATION: (20)..(24)
<223> OTHER INFORMATION: 2'-O-Methyl
<220> FEATURE:
<221> NAME/KEY: modified_base
<222> LOCATION: (25)..(25)
<223> OTHER INFORMATION: dT-C6-NH2
<220> FEATURE:
<221> NAME/KEY: misc_feature
<222> LOCATION: (25)..(25)
<223> OTHER INFORMATION: n is a, c, g, t or u
<220> FEATURE:

```
<221> NAME/KEY: modified_base
<222> LOCATION: (26)..(27)
<223> OTHER INFORMATION: 2'-O-Methyl

<400> SEQUENCE: 7
tttttnagga naccncuuna gcucngg                                              27

<210> SEQ ID NO 8
<211> LENGTH: 25
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (5)..(5)
<223> OTHER INFORMATION: dT-C6-NH2
<220> FEATURE:
<221> NAME/KEY: misc_feature
<222> LOCATION: (5)..(5)
<223> OTHER INFORMATION: n is a, c, g, t or u
<220> FEATURE:
<221> NAME/KEY: modified_base
<222> LOCATION: (8)..(10)
<223> OTHER INFORMATION: 2'-O-Methyl
<220> FEATURE:
<221> NAME/KEY: modified_base
<222> LOCATION: (11)..(11)
<223> OTHER INFORMATION: dT-C6-NH2
<220> FEATURE:
<221> NAME/KEY: misc_feature
<222> LOCATION: (11)..(11)
<223> OTHER INFORMATION: n is a, c, g, t or u
<220> FEATURE:
<221> NAME/KEY: modified_base
<222> LOCATION: (12)..(19)
<223> OTHER INFORMATION: 2'-O-Methyl
<220> FEATURE:
<221> NAME/KEY: modified_base
<222> LOCATION: (20)..(20)
<223> OTHER INFORMATION: dT-C6-NH2
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: modified_base
<222> LOCATION: (21)..(25)
<223> OTHER INFORMATION: 2'-O-Methyl

<400> SEQUENCE: 8
ttttnttucc ncccagcgn gucca                                                 25

<210> SEQ ID NO 9
<211> LENGTH: 26
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (6)..(6)
<223> OTHER INFORMATION: dT-C6-NH2
<220> FEATURE:
<221> NAME/KEY: misc_feature
<222> LOCATION: (6)..(6)
<223> OTHER INFORMATION: n is a, c, g, t or u
```

```
<220> FEATURE:
<221> NAME/KEY: modified_base
<222> LOCATION: (7)..(13)
<223> OTHER INFORMATION: 2'-O-Methyl
<220> FEATURE:
<221> NAME/KEY: modified_base
<222> LOCATION: (14)..(14)
<223> OTHER INFORMATION: dT-C6-NH2
<220> FEATURE:
<221> NAME/KEY: misc_feature
<222> LOCATION: (14)..(14)
<223> OTHER INFORMATION: n is a, c, g, t or u
<220> FEATURE:
<221> NAME/KEY: modified_base
<222> LOCATION: (16)..(16)
<223> OTHER INFORMATION: 2'-O-Methyl
<220> FEATURE:
<221> NAME/KEY: modified_base
<222> LOCATION: (17)..(17)
<223> OTHER INFORMATION: dT-C6-NH2
<220> FEATURE:
<221> NAME/KEY: misc_feature
<222> LOCATION: (17)..(17)
<223> OTHER INFORMATION: n is a, c, g, t or u
<220> FEATURE:
<221> NAME/KEY: modified_base
<222> LOCATION: (18)..(25)
<223> OTHER INFORMATION: 2'-O-Methyl

<400> SEQUENCE: 9
tttttnacca agcntcncca gcacac                                          26

<210> SEQ ID NO 10
<211> LENGTH: 25
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (4)..(4)
<223> OTHER INFORMATION: dT-C6-NH2
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: modified_base
<222> LOCATION: (7)..(9)
<223> OTHER INFORMATION: 2'-O-Methyl
<220> FEATURE:
<221> NAME/KEY: modified_base
<222> LOCATION: (10)..(10)
<223> OTHER INFORMATION: dT-C6-NH2
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: modified_base
<222> LOCATION: (11)..(13)
<223> OTHER INFORMATION: 2'-O-Methyl
<220> FEATURE:
<221> NAME/KEY: modified_base
<222> LOCATION: (14)..(14)
<223> OTHER INFORMATION: dT-C6-NH2
<220> FEATURE:
<221> NAME/KEY: misc_feature
<222> LOCATION: (14)..(14)
<223> OTHER INFORMATION: n is a, c, g, t or u
<220> FEATURE:
<221> NAME/KEY: modified_base
<222> LOCATION: (15)..(16)
```

<223> OTHER INFORMATION: 2'-O-Methyl
<220> FEATURE:
<221> NAME/KEY: modified_base
<222> LOCATION: (18)..(25)
<223> OTHER INFORMATION: 2'-O-Methyl
<220> FEATURE:
<221> NAME/KEY: modified_base
<222> LOCATION: (19)..(19)
<223> OTHER INFORMATION: dT-C6-NH2
<220> FEATURE:
<221> NAME/KEY: misc_feature
<222> LOCATION: (19)..(19)
<223> OTHER INFORMATION: n is a, c, g, t or u

<400> SEQUENCE: 10
tttnttcagn ugancutana auagg         25

<210> SEQ ID NO 11
<211> LENGTH: 27
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (8)..(8)
<223> OTHER INFORMATION: dT-C6-NH2
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: modified_base
<222> LOCATION: (9)..(12)
<223> OTHER INFORMATION: 2'-O-Methyl
<220> FEATURE:
<221> NAME/KEY: modified_base
<222> LOCATION: (13)..(13)
<223> OTHER INFORMATION: dT-C6-NH2
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: modified_base
<222> LOCATION: (14)..(15)
<223> OTHER INFORMATION: 2'-O-Methyl
<220> FEATURE:
<221> NAME/KEY: modified_base
<222> LOCATION: (16)..(16)
<223> OTHER INFORMATION: dT-C6-NH2
<220> FEATURE:
<221> NAME/KEY: modified_base
<222> LOCATION: (17)..(19)
<223> OTHER INFORMATION: 2'-O-Methyl
<220> FEATURE:
<221> NAME/KEY: modified_base
<222> LOCATION: (20)..(20)
<223> OTHER INFORMATION: dT-C6-NH2
<220> FEATURE:
<221> NAME/KEY: misc_feature
<222> LOCATION: (20)..(20)
<223> OTHER INFORMATION: n is a, c, g, t or u
<220> FEATURE:
<221> NAME/KEY: modified_base
<222> LOCATION: (21)..(24)
<223> OTHER INFORMATION: 2'-O-Methyl
<220> FEATURE:
<221> NAME/KEY: modified_base
<222> LOCATION: (25)..(25)
<223> OTHER INFORMATION: dT-C6-NH2
<220> FEATURE:
<221> NAME/KEY: misc_feature

```
<222> LOCATION: (25)..(25)
<223> OTHER INFORMATION: n is a, c, g, t or u
<220> FEATURE:
<221> NAME/KEY: modified_base
<222> LOCATION: (26)..(27)
<223> OTHER INFORMATION: 2'-O-Methyl

<400> SEQUENCE: 11
tttttttncu aanacuguan caucngc                                          27

<210> SEQ ID NO 12
<211> LENGTH: 24
<212> TYPE: DNA
<213> ORGANISM: Artificial Sequence
<220> FEATURE:
<223> OTHER INFORMATION: nucleic acid probe
<220> FEATURE:
<221> NAME/KEY: misc_feature
<222> LOCATION: (1)..(1)
<223> OTHER INFORMATION: 5'-biotin-labeled residue
<220> FEATURE:
<221> NAME/KEY: modified_base
<222> LOCATION: (1)..(1)
<223> OTHER INFORMATION: 2'-O-Methyl
<220> FEATURE:
<221> NAME/KEY: modified_base
<222> LOCATION: (2)..(2)
<223> OTHER INFORMATION: dT-C6-NH2
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: modified_base
<222> LOCATION: (4)..(4)
<223> OTHER INFORMATION: dT-C6-NH2
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: misc_feature
<222> LOCATION: (7)..(7)
<223> OTHER INFORMATION: n is a, c, g, t or u
<220> FEATURE:
<221> NAME/KEY: modified_base
<222> LOCATION: (8)..(12)
<223> OTHER INFORMATION: 2'-O-Methyl
<220> FEATURE:
<221> NAME/KEY: modified_base
<222> LOCATION: (13)..(13)
<223> OTHER INFORMATION: dT-C6-NH2
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: modified_base
<222> LOCATION: (14)..(21)
<223> OTHER INFORMATION: 2'-O-Methyl
<220> FEATURE:
<221> NAME/KEY: modified_base
<222> LOCATION: (22)..(22)
<223> OTHER INFORMATION: dT-C6-NH2
<220> FEATURE:
<221> NAME/KEY: misc_feature
<222> LOCATION: (22)..(22)
<223> OTHER INFORMATION: n is a, c, g, t or u
<220> FEATURE:
<221> NAME/KEY: modified_base
<222> LOCATION: (23)..(24)
<223> OTHER INFORMATION: 2'-O-Methyl

<400> SEQUENCE: 12
untnttnaaa aanggggcaa anaa                                             24
```